[](#)

United States Patent
Scheidt et al.

(10) Patent No.: US 8,912,341 B2
(45) Date of Patent: Dec. 16, 2014

(54) ENANTIOSELECTIVE N-HETEROCYCLIC CARBENE-CATALYZED ANNULATION REACTIONS WITH IMIDAZOLIDINONES

(71) Applicant: Northwestern University, Evanston, IL (US)

(72) Inventors: Karl A. Scheidt, Evanston, IL (US); Elizabeth O. McCusker, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/999,125

(22) Filed: Jan. 16, 2014

(65) Prior Publication Data

US 2014/0206886 A1   Jul. 24, 2014

Related U.S. Application Data

(60) Provisional application No. 61/753,509, filed on Jan. 17, 2013, provisional application No. 61/753,310, filed on Jan. 16, 2013.

(51) Int. Cl.
*C07D 491/052* (2006.01)

(52) U.S. Cl.
CPC .................................. *C07D 491/052* (2013.01)
USPC ...................................... 548/303.1; 548/324.1

(58) Field of Classification Search
USPC ....................................................... 548/303.1
See application file for complete search history.

(56) References Cited

PUBLICATIONS

Raup, D.E.A. et al., "Cooperative catalysis by carbenes and Lewis acids in a highly stereoselective Route to y-lactams", Nat. Chem. 2010, 2(9), 766-771.
Pangborn, A.B. et al., "Safe and convenient procedure for solvent purification" Organometallics 1996, 15(5) 1518-1520.
Avery, T.D. et al., "1,2-dioxines containing tethered hydroxyl functionality as convenient precursors for pyran syntheses", J. Org. Chem. 2005, 70(21), 8344-8351.
Kaushik, D. et al., Synthesis of (substituted benzamidostryryl) IH-benzimidazoles and their screening for anti-inflammatory activity, Med. Chem. Res. 2012, 21, 459-467.
Kidwai, A.R. et al., "A new method for the synthesis of amino acids. Synthesis of amino acids and their derivatives through 2,4-disubstituted 2-Imidazolin-5-ones", J. Org. Chem. 1962, 27(12), 4527-4531.
Momose, Y. et al., "Novel 5-substituted 2,4-thiazolidinedione and 2,4-oxazolidinedione derivatives as insulin sensitizers with antidiabetic activities", J. Med. Chem. 2002, 45(7), 1518-1534.

*Primary Examiner* — Laura L. Stockton
(74) *Attorney, Agent, or Firm* — Reinhart Boerner Van Deuren s.c

(57) ABSTRACT

Enantiomeric bicyclic lactone compounds as can be prepared via an N-heterocyclic carbene-catalyzed annulation reaction.

20 Claims, No Drawings

ENANTIOSELECTIVE N-HETEROCYCLIC CARBENE-CATALYZED ANNULATION REACTIONS WITH IMIDAZOLIDINONES

This application claims priority benefit from application Ser. No. 61/753,310 filed Jan. 16, 2013 and application Ser. No. 61/753,509 filed Jan. 17, 2013—each of which is incorporated herein by reference in its entirety.

This invention was made with government support under grant number GM073072 awarded by the National Institutes of Health. The government has certain rights in the invention.

BACKGROUND OF THE INVENTION

The development of efficient strategies for the stereoselective construction of privileged heterocyclic systems is an important objective in chemical synthesis and pharmaceutical sciences. Over the last decade, N-heterocyclic carbene (NHC) catalysis has provided opportunities for the development of new transformations based on polarity reversal or Umpolung reactivity. The exploration of these unconventional reactivity patterns with new electrophilic coupling partners facilitates advances in synthesis and provides access to bioactive natural products and unique, drug-like scaffolds. Substituted imidazoles are a privileged structural motif that is prevalent in pharmaceutical small molecules with diverse biological activities, including inflammation, HIV, depression, and various other disease areas.

There are several methods for the synthesis of substituted imidazoles and one approach involves the conversion of readily accessible imidazolidinones to the related imidazoles through functional group transformation. However, unlike the related oxazolones, new asymmetric methods involving imidazolidinones are scarce in the literature. There have been several recent reports involving the use of alkylidene oxazolones in enantioselective processes, likely due to the ability to access unnatural amino acids from these readily available precursors, but the related alkylidene imidazolidinones have received less attention. It was thought that Michael acceptors with such a heterocyclic framework combined with α,β-unsaturated aldehydes under carbene catalysis conditions could provide access to novel chiral imidazoles through a formal [4+2] annulation, but the use of such electron rich conjugate acceptors has not been investigated in the preparation of bicyclic dihydropyranoimidazolones.

SUMMARY OF THE INVENTION

In light of the foregoing, it is an object of the present invention to provide various dihydropyranoimidazolone compounds and method(s) for their preparation, thereby addressing various issues relating to the prior art, including those outlined above. It will be understood by those skilled in the art that one or more aspects of this invention can meet certain objectives, while one or more aspects can meet certain other objectives. Each objective will not apply equally in all its respects, to every aspect of this invention. As such, the following objects can be viewed in the alternative to any one aspect of this invention.

It is an object of this invention to provide a range of dihydropyrano[2,3-d]imidazol-5(3H)-one compounds and an enantioselective methodology for their preparation. Such compounds are potentially bioactive and can be employed in natural product synthesis and/or in the development of pharmaceutical agents.

It can also be another aspect of this invention to utilize the aforementioned compounds in the synthesis of chiral imidazoles which also have potential bioactivity.

It can also be an object of this invention to provide a methodology which is operationally simple and employs starting materials either commercially available or easily prepared.

It can also be an object of this invention, alone or in conjunction with one or more of the preceding objectives, to provide a synthetic methodology able to employ and tolerate a wide range of starting materials, and functional groups thereon, en route to a corresponding range of imidazolone products and imidazole derivatives available therefrom.

Other objects, features, benefits and advantages of the present invention will be apparent from the summary and the following descriptions of certain embodiments, and will be readily apparent to those skilled in the art having knowledge of various synthetic methods and techniques. Such objections, features, benefits and advantages will be apparent from the above as taken into conjunction with the accompanying examples, data, figures and all reasonable inferences to be drawn therefrom.

In part, the present invention can be directed to compounds of a formula

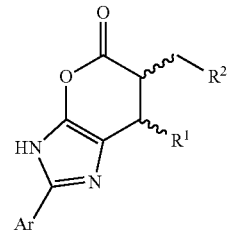

and salts thereof. In certain such compounds, Ar can be selected from aryl and substituted aryl moieties, with such Ar substituents as can be selected from but not limited to alkyl, alkoxy, halo and haloalkyl substituents and combinations thereof; and $R^1$ and $R^2$ can be independently selected from H, alkyl, substituted alkyl, cycloalkyl, substituted cycloalkyl, aryl, substituted aryl, heteroaryl and substituted heteroaryl moieties, with such $R^1$ and $R^2$ substituents as can be independently selected from but not limited to alkyl, alkoxy, halo and haloalkyl substituents and combinations thereof. Regardless of Ar and $R^1$-$R^2$ identity, such a compound can be enantioenriched with respect to the following diastereomer

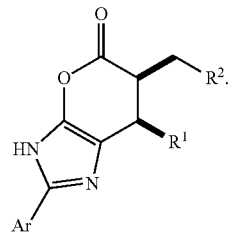

In part, the present invention can be directed to a method for asymmetric synthesis of compounds of a formula

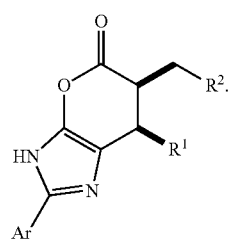

Generally, such a method can comprise reacting an alkylidene imidazolidinone of a structure

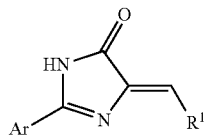

and an α,β-unsaturated aldehyde of a structure

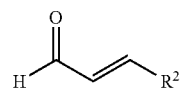

in the presence of a triazolium carbene catalyst precursor, as illustrated below, under conditions of the sort described herein. Each of Ar, $R^1$ and $R^2$ of such starting materials can be as described above or discussed elsewhere herein.

Without limitation, this invention can be directed to a method of preparing a bicyclic lactone compound. Such a method can comprise providing a mixture of a heterocyclic alkylidene imidazolidinone, a triazolium N-heterocyclic carbene catalyst precursor compound and a base component, such an alkylidene imidazolidinone of a formula

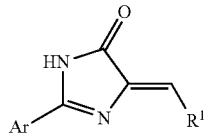

wherein Ar can be selected from aryl and substituted aryl moieties, with Ar substituents as can be selected from alkyl, alkoxy, halo and haloalkyl substituents and combinations thereof, and $R^1$ can be selected from aryl, substituted aryl, heteroaryl, substituted heteroaryl, alkyl and cycloalkyl moieties, with $R^1$ substituents as can be selected from alkyl, alkoxy, halo and haloalkyl substituents and combinations thereof; and introducing to such a mixture an α,β-unsaturated aldehyde in the presence of an acid component, such an aldehyde of a formula

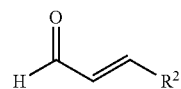

wherein $R^2$ can be selected from H, alkyl, cycloalkyl, aryl, substituted aryl, heteroaryl and substituted heteroaryl moieties, with $R^2$ substituents as can be selected from alkyl, alkoxy and halo substituents and combinations thereof, to provide a bicyclic lactone compound of a formula or a salt thereof

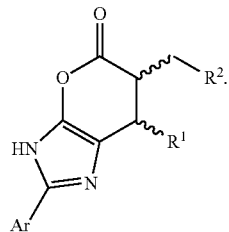

In certain embodiments, such an acid component can be acetic acid. In certain such embodiments, such a base component can be an acetate such as, without limitation, an ammonium acetate. Regardless, Ar can be substituted aryl and an Ar substituent can be selected from fluoro- and chloro- substituents. In certain such embodiments, such a substituent can be an ortho-position on such an aryl moiety.

Alternatively, without limitation, this invention can be directed to a method of using a heterocyclic conjugate acceptor component to prepare a bicyclic lactone compound of a formula

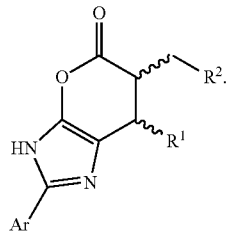

Such a method can comprise providing a mixture of a heterocyclic alkylidene imidazolidinone, a triazolium N-heterocyclic carbene catalyst precursor compound and a base components, such an alkylidene imidazolidinone of a formula

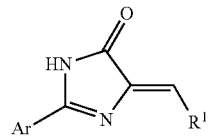

wherein Ar can be selected from aryl and substituted aryl moieties, with Ar substituents as can be selected from alkyl, alkoxy, halo and haloalkyl substituents and combinations thereof, and $R^1$ can be selected from aryl, substituted aryl, heteroaryl, substituted heteroaryl, alkyl and cycloalkyl moieties, with $R^1$ substituents as can be selected from alkyl, alkoxy, halo and haloalkyl substituents and combinations thereof; introducing to such a mixture an α,β-unsaturated aldehyde in the presence of an acid component, such an aldehyde of a formula

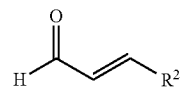

wherein $R^2$ can be selected from H, alkyl, cycloalkyl, aryl, substituted aryl, heteroaryl, substituted heteroaryl moieties, with $R^2$ substituents as can be selected from alkyl, alkoxy and halo substituents and combinations thereof, to couple such components; and intramolecular O-acylation of such an imidazolidinone to provide such a bicyclic lactone compound or a salt thereof. In certain non-limiting embodiments, acid and base components can be as discussed above or illustrated elsewhere herein. Likewise, Ar, $R^1$ and $R^2$ (and any substituents(s) thereof) can be as discussed above or illustrated elsewhere herein.

DETAILED DESCRIPTION OF CERTAIN EMBODIMENTS

Throughout, where compounds or compositions are described as having, including, or comprising specific components, or where processes are described as having, including, or comprising specific process steps, it is contemplated that compounds of the present teachings also consist essentially of, or consist of, the recited moieties and/or substituents thereof, that compositions of the present teachings also consist essentially of, or consist of, the recited components, and that the processes of the present teachings also consist essentially of, or consist of, the recited process steps.

Where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

Throughout, structures may or may not be presented with chemical names. Where any question arises as to nomenclature, the structure prevails.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and can be optionally substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which can be optionally substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which can be optionally substituted as described herein.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and can be optionally substituted as described herein.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, ten-butyl). In some embodiments, alkyl groups can be substituted as described herein. An alkyl group is generally not substituted with another alkyl group, an alkenyl group, or an alkynyl group, but can be substituted with other substituents (e.g., halo, as described below, amino, cyano, etc.) of the sort described herein.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula —$C_sH_{2s+1-t}X^0_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxy, hexoxy groups, and the like. The alkyl group in the —O-alkyl group can be substituted as described herein. For example, an —O-haloalkyl group is considered within the definition of "alkoxy" as used herein.

As used herein, "arylalkyl" refers to an -alkyl-aryl group, where the arylalkyl group is covalently linked to the defined chemical structure via the alkyl group. An arylalkyl group is within the definition of a —Y—$C_{6-14}$ aryl group, where Y is defined as a divalent alky group that can be optionally substituted as described herein. An example of an arylalkyl group is a benzyl group (—$CH_2$—$C_6H_5$). An arylalkyl group can be optionally substituted, i.e., the aryl group and/or the alkyl group, can be substituted as disclosed herein.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or Spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S- dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., $-C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below

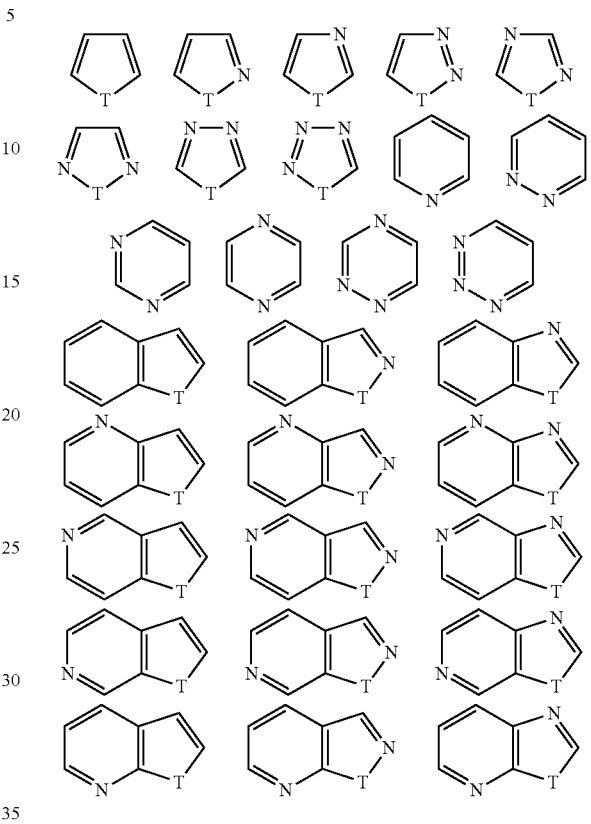

where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

As relates to certain non-limiting embodiments of this invention, the NHC-catalyzed combination of α,β-unsaturated aldehydes with alkylidene imidazolidinones can afford enantioenriched bicyclic lactones—such syntheses as can be considered through a formal [4+2] annulation. The subsequent treatment of the lactone products with dilute acid followed by acylation affords a second class of 5-oxyimidazoles. This convergent, stereoselective and modular approach to these two unique classes of imidazoles allows for incorporation of a wide range of functionality through appropriate choice of the imidazolidinone and aldehyde coupling partners.

Initially, phenyl substituted imidazolidinone 4a was combined with cinnamaldehyde in the presence of triethylamine and azolium A. Under these conditions, a modest 33% conversion of the imidazolidinone to lactone 5a (Table 1) was observed. Encouraged by this lead, different aryl-substituted imidazolidinones were prepared and explored in this NHC-catalyzed annulation. Due to the limited solubility of imidazolidinone 4a in typical organic solvents, it was hypothesized that this physical characteristic was responsible for the low conversion. Initial exploration of imidazolidinones 4b-d, bearing a substituent at the 4-position, provided no improvement in solubility or conversion relative to 4a. The synthesis of imidazolidinones 4e-h with ortho-substitution on the aromatic ring provided more interesting results.

TABLE 1

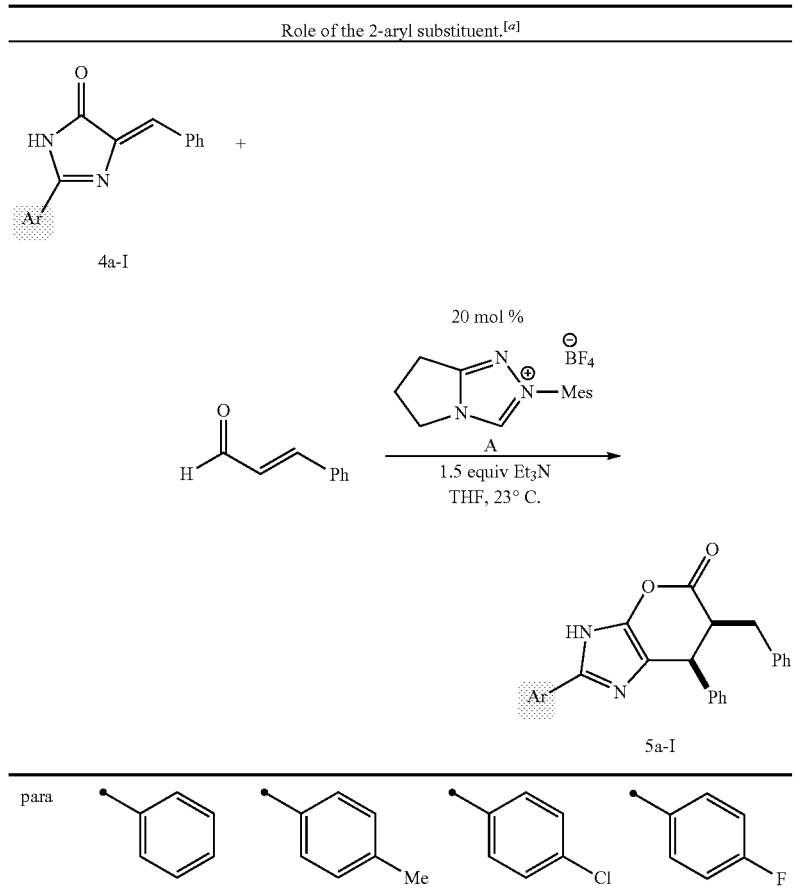

TABLE 1-continued

Role of the 2-aryl substituent.[a]

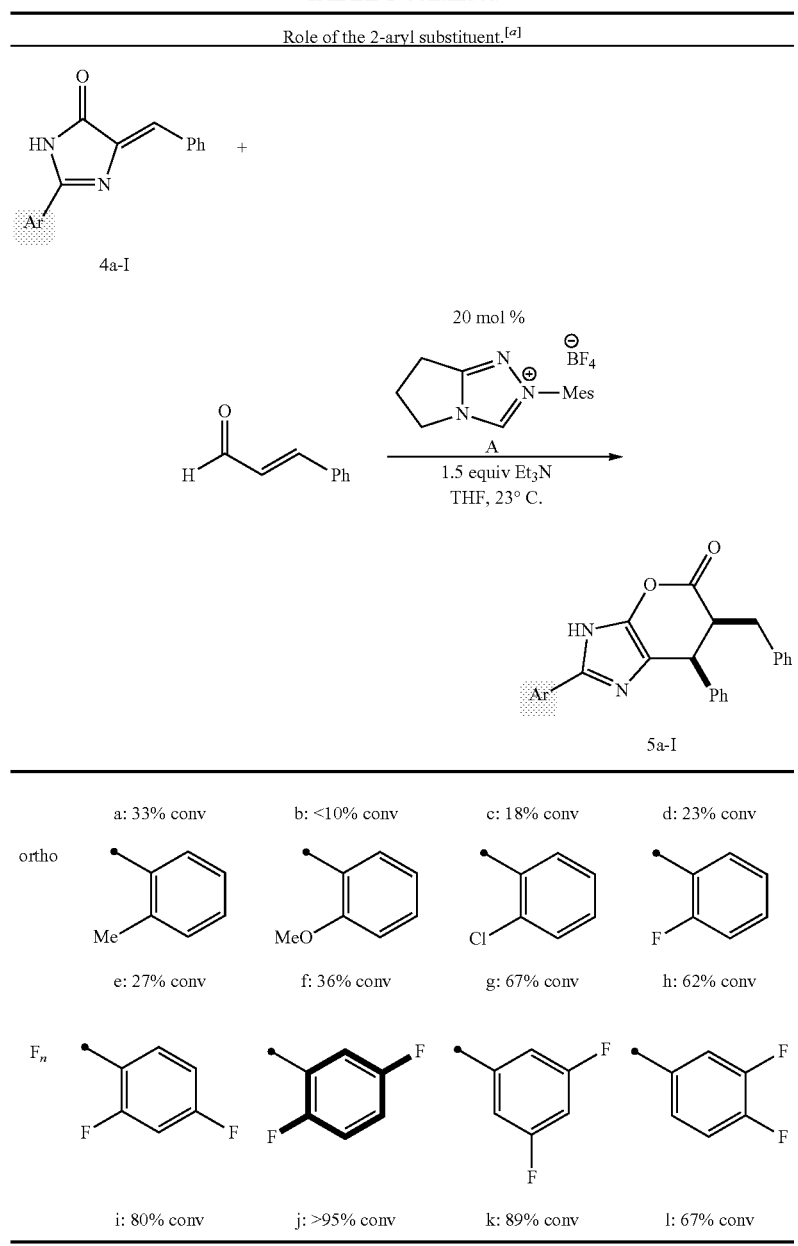

[a]Determined by $^1$H NMR spectroscopy (500 MHz) of the unpurified reaction.

While the ortho-substituent increased solubility, resulting in a homogeneous reaction mixture for substrates 4e-h, higher levels of conversion were observed in the presence of electron-withdrawing (4g-h) compared to electron-donating groups (4e-f). Prompted by these results, a number of 2-aryl imidazolidinones bearing additional electron withdrawing substituents (e.g., a difluoroaryl group) were evaluated: as shown in Table 1, with imidazolidinones 4i-k >80% conversion was achieved.

At this point, 2,5-difluorophenyl substituted imidazolidinone 4j was selected for further investigation of the reaction conditions. With 15 mol % azolium A and triethylamine as the base, the reaction between imidazolidinone 4j and cinnamaldehyde afforded lactone 5j as the major product, but also gave rise to a significant amount of spirocycle 6j as a 1:1 mixture of diastereomers (Table 2, entry 1). The formation of spirocycle 6j is believed to result from a formal [3+2] annulation between the imidazolidinone and cinnamaldehyde.

The use of chiral triazolium precatalyst B did not significantly improve the ratio of 5j:6j, but the lactone (5j) was generated with excellent enantioselectivity (95:5 er). Similar results were obtained with the 2,6-diethylphenyl substituted triazolium C, and due to a reproducible increase in enantioselectivity (98:2 er), this catalyst was employed in further optimization endeavors (entry 3). (See, D. E. A. Raup, B. Cardinal-David, D. Holte, K. A. Scheidt, Nat. Chem. 2010, 2, 766-771.) Interestingly, the homoenolate driven process that generates spirocycle 6j proceeds with significantly lower enantioselectivity (70:30 er, results not shown). Given the excellent selectivity for the formal [4+2] process, efforts were focused on improving selectivity for lactone 5j.

TABLE 2

Optimization of reaction conditions.

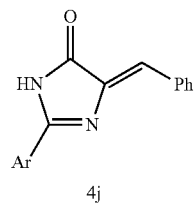

| entry | NHC | base (equiv) | conv[a] | 5/6[a] | dr major[a] | er[b] |
|---|---|---|---|---|---|---|
| 1 | A | Et$_3$N (1.5) | 85 | 55:45 | 10:1 | — |
| 2 | B | Et$_3$N (1.5) | 84 | 63:37 | 10:1 | 95:5 |
| 3 | C | Et$_3$N (1.5) | 75 | 66:34 | 10:1 | 98:2 |
| 4[c] | C | Et$_3$N (1.5) | 81 | 82:18 | 11:1 | 98:2 |
| 5 | C | NaOAc (0.3) | 68 | 69:31 | 10:1 | 98:2 |
| 6 | C | KOAc (0.3) | 44 | 76:24 | 10:1 | 98:2 |
| 7 | C | CsOAc (0.3) | 96 | 71:29 | 1.5:1 | 96:4 |
| 8 | C | $^n$Bu$_4$NOAc (0.3) | 94 | 82:18 | 6:1 | 98:2 |
| 9[c] | C | $^n$Bu$_4$NOAc (0.3) | 96(73)[d] | 91:9 | 6:1 | 98:2 |

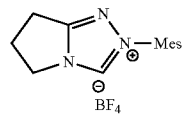

A

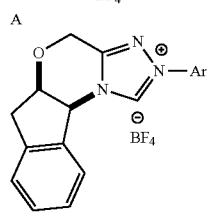

B: Ar = Mes
C: Ar = 2,6-Et$_2$Ph

[a]Determined by $^1$H NMR spectroscopy (500 MHz) of the unpurified reaction.
[b]Enantiomeric excess determined by HPLC.
[c]1.0 equiv acetic acid as an additive.
[d]Isolated yield.

It was hypothesized that an increase in the rate of the initial β-protonation would increase the product ratio to favor lactone 5j. Use of a Breasted acid additive was employed to explore this possible modulation between the formal [4+2] and [3+2] manifolds. These studies indicated that acetic acid indeed improved the ratio of 5:6 in favor of lactone 5j while maintaining the high levels of enantioselectivity (Table 2, entry 4). Based on this result, the use of acetate bases with varying counterions was investigated (entry 5-8). Different acetate bases produced lactone 5j with varying levels of selectivity, with tetra-n-butylammonium acetate providing the highest levels of conversion and selectivity (82:12 for 5j/6j, 6:1 dr, entry 8). Finally, the use of acetic acid in conjunction with tetra-n-butylammonium acetate further improved the level of selectivity for lactone 5j over spirocycle 6j, with lactone 5j isolated in 73% yield and 98:2 enantiomeric ratio (entry 9).

With the optimized reaction conditions established, the scope of this NHC-enolate driven formal annulation with various α,β-unsaturated aldehydes was explored. Electron-donating substituents were well tolerated at all positions of the aromatic ring, affording the lactone products in good yield and diastereoselectivity and excellent enantioselectivity (Table 3, entry 2-5). Aldehydes bearing electron withdrawing groups were also explored (entry 6-9), with lactones 11-14 formed in moderate to good yield and selectivities. Various other aromatic substituents, including 2-napthyl and 2-furyl, also performed well in the reaction.

TABLE 3

Aldehyde reaction scope.[a]

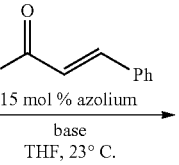

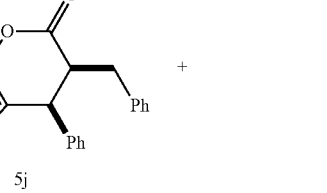

| entry | R | yield (%)[b] | dr[c] | er (major)[d] |
|---|---|---|---|---|
| 1 | Ph (5j) | 73 | 6:1 | 98:2 |
| 2 | 4-Me—C$_6$H$_4$ (7) | 82 | 6:1 | 99:1 |
| 3 | 3-Me—C$_6$H$_4$ (8) | 61 | 2:1 | 97:3 |
| 4 | 4-OMe—C$_6$H$_4$ (9) | 76 | 7:1 | 99:1 |
| 5 | 2-OMe—C$_6$H$_4$ (10) | 61 | 7:1 | 96:4 |
| 6 | 4-Br—C$_6$H$_4$ (11) | 64 | 2:1 | 96:4 |
| 7 | 4-Cl—C$_6$H$_4$ (12) | 58 | 7:1 | 98:2 |
| 8 | 3-Cl—C$_6$H$_4$ (13) | 46 | 2:1 | >99:1 |
| 9 | 2-Cl—C$_6$H$_4$ (14) | 48 | 2.5:1 | 92:8 |
| 10 | 2-naphthyl (15) | 71 | 2:1 | 96:4 |
| 11 | 2-furyl (16) | 66 | 3:1 | 98:2 |
| 12 | n-propyl (17) | 90 | >20:1 | >99:1 |
| 13 | Me (18) | 80 | >20:1 | >99:1 |
| 14 | cyclohexyl (19) | 56 | >20:1 | 98:2 |
| 15 | H (20) | 42 | >20:1 | >99:1 |

[a]See examples, below, for details.
[b]Isolated yield after chromatography.
[c]Determined by $^1$H NMR (500 MHz) or $^{19}$F NMR (376 MHz) spectroscopy.
[d]Enantiomeric ratio determined by HPLC.

β-alkyl substituted enals were observed as competent substrates in this transformation. With 2-hexenal and crotonaldehyde, the reaction proceeded to full conversion to afford lactones 17 and 18 in 90% and 80% yield, respectively, and with high diastereo- and enantioselectivity (entry 12-13). Despite the fact that the reactions involving the cyclohexyl-substituted enal and the highly reactive parent aldehyde, acrolein, did not reach full conversion (>60% over 48 h), lactones 19 and 20 were nevertheless obtained in moderate yield and excellent selectivity (entry 14-15).

Structural modification of the aryl and alkylidene components of the imidazolidinone was also explored (Table 4). Several of the aforementioned imidazolidinones were employed in the annulation reaction under the optimized reaction conditions. With chiral triazolium C, imidazolidinones 4h and 4i displayed relatively low reactivity, but were converted to the corresponding lactones in good yield and selectivity over prolonged reaction times (>70% conversion over 48 h). In addition, the 3,5-trifluoromethyl substrate also performed well in this reaction. Variation of the alkylidene substituent revealed that several aromatic groups can be employed at this position, including those with electron withdrawing and donating substituents. In addition, the incorporation of an alkyl group was achieved and enabled the preparation of various alkyl substituted lactones with excellent diastereo- and enantioselectivity. Of particular interest is the synthesis of bis-alkyl substituted lactone 26 in 59% yield and >99:1 enantiomeric ratio.

TABLE 4

Imidazolidinone Reaction Scope.[a]

5h (65% yield)
2.5:1 dr (98:2 er)

5i (62% yield)
4:1 dr (98:2 er)

21 (57% yield)
5:1 dr (>99:1 er)

TABLE 4-continued

Imidazolidinone Reaction Scope.[a]

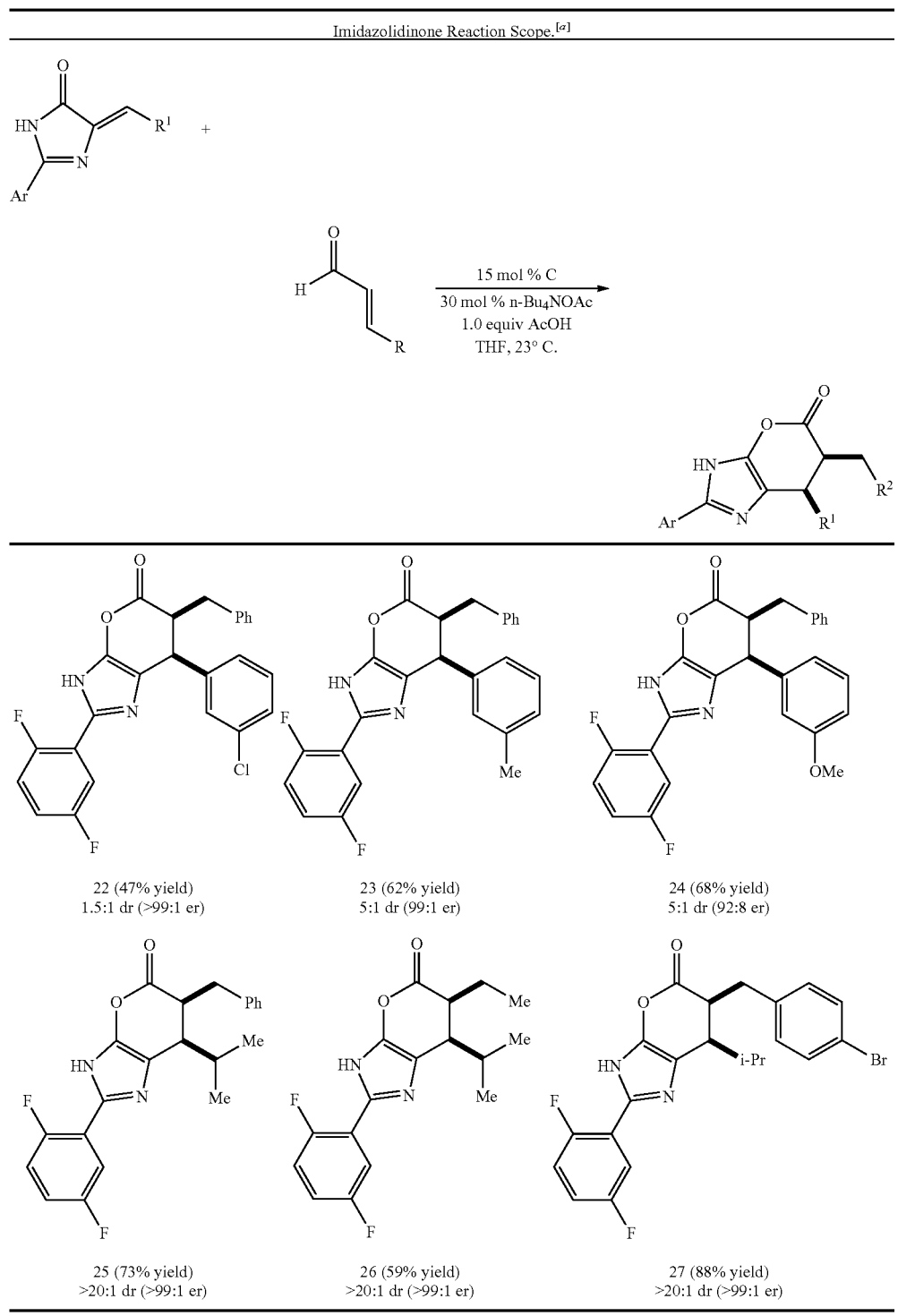

| 22 (47% yield) | 23 (62% yield) | 24 (68% yield) |
| 1.5:1 dr (>99:1 er) | 5:1 dr (99:1 er) | 5:1 dr (92:8 er) |

| 25 (73% yield) | 26 (59% yield) | 27 (88% yield) |
| >20:1 dr (>99:1 er) | >20:1 dr (>99:1 er) | >20:1 dr (>99:1 er) |

[a]See examples, below, for details. Yield of isolated product after chromatography.
Diastereomeric ratios determined by ¹H NMR (500 MHz) of ¹⁹F NMR (376 MHz) spectroscopy.
Enantiomeric ratio determined by HPLC.

Current understanding of such an annulation is that the lactone products can be obtained through either a stepwise or concerted [4+2] process, while the observed spirocycle (6) arises from a divergent formal [3+2] annulation pathway. Based on previous computational reports in the literature and independent observations, here, a stepwise process for this specific reaction is considered. Without limitation to any one theory or mode of operation, a proposed catalytic cycle for both the lactone and spirocycle products begins with addition of the NHC to cinnamaldehyde to generate the extended Breslow intermediate. At this point, the NHC-bound homoenolate can undergo either β-protonation to generate catalytic enol intermediate IV, or conjugate addition to the imidazolidinone to arrive at an alternate catalytic enol (VII). In the presence of an acid source, it is proposed that the rate of β-protonation is increased to favor formation of the formal [4+2] annulation product. In this case, the generation of enol II then promotes approach of the imidazolidinone from the back face and subsequent coordination through a hydrogen bonding interaction, resulting in an organized transition state (III). Following carbon-carbon bond formation, azolium IV can undergo O-acylation to release the NHC catalyst and furnish the lactone product (5).

Alternatively, if β-protonation is slow, a mixture of products may be obtained due to a competing [3+2] annulation pathway. In this case, it is proposed that the imidazolidinone can approach in either a synclinal (VI) or antiperiplanar fashion (not shown), and the lack of differentiation between these two transition states results in the poor diastereoselectivity (1:1) observed. Following carbon-carbon bond formation to generate hydroxy imidazole-terminated enol VII, tautomerization occurs to give rise to acyl azolium VIII, which then presumably undergoes atypical C-acylation vs. O-acylation to afford 6.

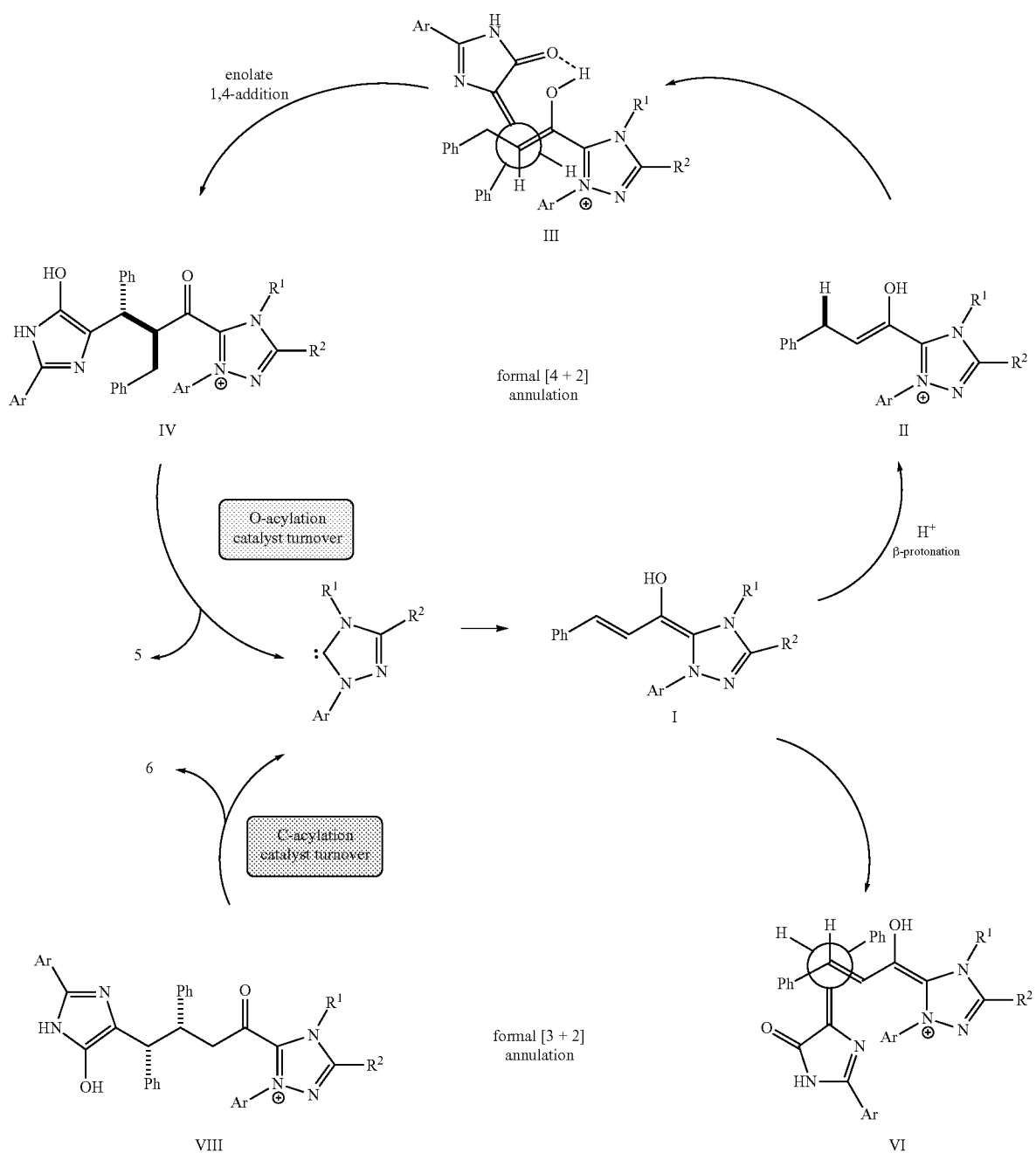

Scheme 1. Proposed Reaction Pathway.

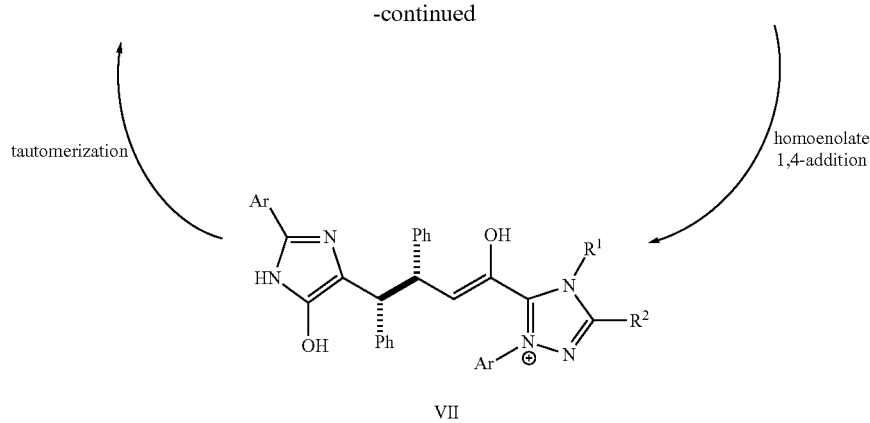

To illustrate but one application of this invention, the present bicyclic lactone compounds can be readily converted to a class of 5-oxyimidazoles through acid-catalyzed opening of the lactone followed by acylation. In this manner, for example, imidazole 28 was generated in 66% yield over the two-step sequence (Scheme 2). Likewise, a wide range of acylating agents can be employed to access various 5-acylimidazoles.

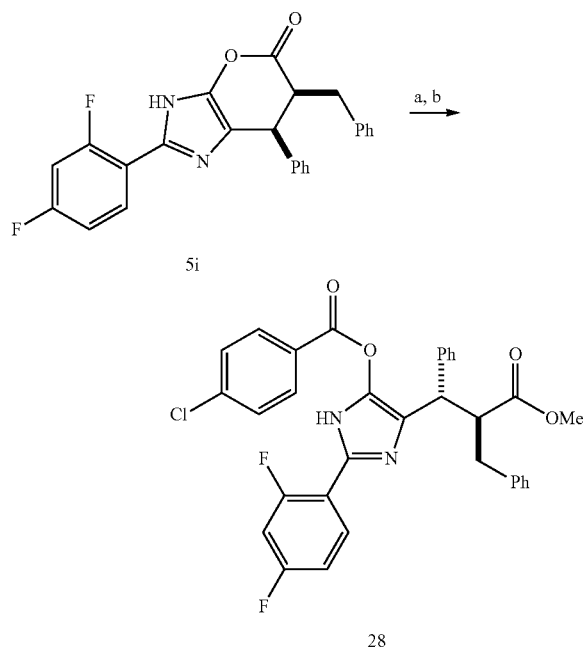

[a] See examples, below, for details. Reagents and conditions: (a) 5% formic acid in MeOH, 65° C., 70% (b) Et₃N, 4-chlorobenzoyl chloride, THF, 23° C., 94%

As demonstrated herein, this invention provides a highly selective NHC-catalyzed formal annulation of α,β-unsaturated aldehydes with imidazolidinones. An electron-withdrawing 2-aryl substituent on the imidazolidinone can activate the conjugate acceptor and achieve high conversion. In addition, a Brønsted acid can be employed to achieve chemoselectivity. This present enantioselective methodology provides a distinct approach to substituted imidazoles, whereby incorporation of various substituents can be achieved through judicious choice of the imidazolidinone and aldehyde starting materials.

EXAMPLES OF THE INVENTION

The following non-limiting examples and data illustrate various aspects and features relating to the compounds and/or methods of the present invention, including the preparation of various bicyclic lactone compounds, as are available through the enantioselective synthetic methodologies described herein. In comparison with the prior art, the present compounds and/or methods provide results and data which are surprising, unexpected and contrary thereto. While the utility of this invention is illustrated through the use of several imidazolidinone and unsaturated aldehyde starting materials and moieties and/or substituents thereof, it will be understood by those skilled in the art that comparable results are obtainable with various other starting materials, corresponding moieties and substituents thereof, as are commensurate with the scope of this invention.

General Information

All reactions were carried out under a nitrogen atmosphere in oven-dried glassware with magnetic stirring. THF was purified by passage through a bed of activated alumina. (See, A. B. Pangborn, M. A. Giardello, R. H. Grubbs, R. K. Rosen, F. J. Timmers, *Organometallics* 1996, 15, 1518.) Reagents were purified prior to use unless otherwise stated following the guidelines of Perrin and Armarego. (See, D. D. Perrin, W. L. Armarego, *Purification of Laboratory Chemicals;* 3rd Ed., Pergamon Press, Oxford. 1988.)

Purification of reaction products was carried out by flash chromatography using EM Reagent or Silicycle silica gel 60 (230-400 mesh). Analytical thin layer chromatography was performed on EM Reagent 0.25 mm silica gel 60-F plates. Visualization was accomplished with UV light and ceric ammonium nitrate stain or potassium permanganate stain followed by heating. Infrared spectra were recorded on a Bruker Tensor 37 FT-IR spectrometer. $^{1}$H-NMR spectra were recorded on a Bruker Avance 500 MHz w/ direct cryoprobe (500 MHz) spectrometer and are reported in ppm using solvent as an internal standard (CDCl₃ at 7.26 ppm, d₆-DMSO at 2.50 ppm). Data are reported as (ap=apparent, s=singlet, d=doublet, t=triplet, q=quartet, m=multiplet, b=broad; coupling constant(s) in Hz; integration). Proton-decoupled $^{13}$C-NMR spectra were recorded on a Bruker Avance 500 MHz w/ direct cryoprobe (126 MHz) spectrometer and are reported in ppm using solvent as an internal standard (CDCl₃ at 77.0 ppm, d6-DMSO at 39.5 ppm). Mass spectra data were obtained on a Waters Acquity Single Quadrupole ESI Spectrometer and Micromass Quadro II Spectrometer.

Trans-cinnamaldehyde, crotonaldehyde, 2-methoxy-cinnamaldehyde, 3-(2-furyl)-acrolein, 2-hexenal, and acrolein were obtained from commercial sources (Sigma Aldrich, Acros, Oakwood). All other cinnamaldehyde derivatives were prepared by a Wittig, oxidation, and reduction sequence. (See, T. D. Avery, D. Caiazza, J. A. Culbert, D. K. Taylor, E. R. T. Tiekink, *J. Org. Chem.* 2005, 70, 8344; and Y. Momose, T. Maekawa, T. Yamano, M. Kawada, H. Odaka, H. Ikeda, T. Sohda, *J. Med. Chem.* 2002, 45, 1518.) N-aroyl glycine derivatives were prepared according to the procedure described by Kaushik and coworkers. (See, D. Kaushik, S. A. Khan, G. Chawla, *Med. Chem. Res.* 2011, 21, 459.)

Example 1

General Procedure for Synthesis of Imidazolidinone Derivatives

Method A:

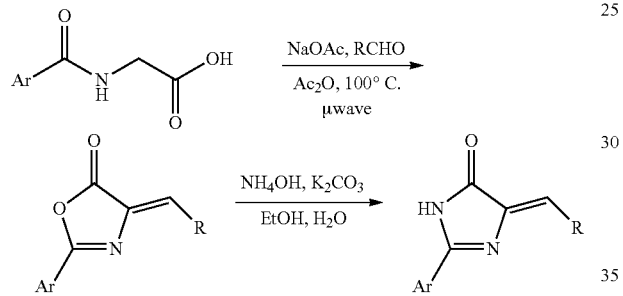

Into Biotage microwave vial was added glycine derivative (1.0 equiv), aldehyde (1.0 equiv), acetic anhydride (2.0 equiv), and sodium acetate (0.3 equiv). The vial was capped and placed in a Biotage Initiator microwave reactor for 5 minutes at 100° C. The vial was removed from the microwave after cooling and the lid removed. The resultant yellow solid was transferred to an Erlenmeyer flask with ethanol and stirred for 30 minutes. The product was collected by vacuum filtration to give the oxazolone as a yellow solid. Into a round bottom flask equipped with a magnetic stirbar and reflux condenser was added the oxazolone followed by ethanol and water (2:1 EtOH/H2O, 0.5 M). Ammonium hydroxide (5 equiv) was added and the reaction was heated to 80° C. Upon dissolution of the solid, potassium carbonate (0.9 equiv) was added and the temperature increased to 100° C. The reaction was stirred for 3 hours with periodic addition of ammonium hydroxide (5 equiv) until no more yellow solid crashed out of solution. The solid was collected by vacuum filtration and recrystallized with ethanol and water to afford the imidazolidinones as a yellow solid.

Example 2

Method B

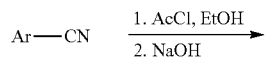

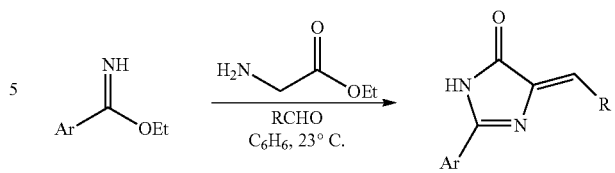

The benzonitrile (1.0 equiv) was dissolved in ethanol (200 proof, 8.0 equiv) and cooled to 0° C. Acetyl chloride (4.0 equiv) was added dropwise via addition funnel to the reaction mixture. Upon completion of addition, the flask was stoppered and allowed to warm to room temperature and stir overnight. The reaction mixture was concentrated and then diethyl ether was added and the slurry stirred for 1 hour. The white solid was collected by vacuum filtration. The imidic acid ethyl ester and glycine ethyl ester hydrochloride salts were converted into the free esters following the procedure of detailed by Kidwai and Devasia. (See, A. R. Kidwai, G. M. Devasia, *J. Org. Chem.* 1962, 27, 4527-4531.) The imidic acid ethyl ester (1.125 equiv), glycine ethyl ester (0.17 equiv), anhydrous benzene (2.2 M), and the aldehyde (1.0 equiv) were quickly mixed and kept closed in a flask at room temperature with occasional shaking. After 72-96 h the mixture completely solidified into a yellow mass with a red tinge. The crude products were collected by vacuum filtration and recrystallized with hot ethanol and water to afford the pure imidazolidinones as a yellow solid.

Example 3

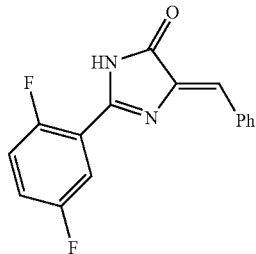 [SMILES: O=C1NC(c2cc(F)ccc2F)=N/C1=C\c1ccccc1]

(Z)-4-benzylidene-2-(2,5-difluorophenyl)oxazol-5(4H)-one (4j)

Prepared according to Method A using 2-(2,5-difluorobenzamido)acetic acid (3.0 g, 13.94 mmol) and benzaldehyde. The crude solid was recrystallized with hot ethanol to afford imidazolidinone 1j as a bright yellow solid (1.28 g, 32%). Analytical data for 4j: $^1$H NMR (500 MHz, CDCl$_3$) δ 9.04 (br s, 1H), 8.28-8.22 (m, 2H), 8.16 (ddd, J=8.8, 5.7, 3.2 Hz, 1H), 7.52-7.42 (m, 3H), 7.27 (s, 1H), 7.25-7.18 (m, 2H); $^{13}$C NMR (CDCl$_3$, 126 MHz) δ 171.3, 158.9 (d, $J_{CF}$=245.0 Hz), 157.3 (d, $J_{CF}$=248.7 Hz), 154.1, 138.0, 134.0, 132.7, 130.9, 129.9, 128.9, 121.0 (dd, $J_{CF}$ 24.8, 9.6 Hz), 118.0 (dd, $J_{CF}$=26.0, 8.4 Hz), 117.3 (dd, $J_{CF}$=12.0, 8.4 Hz), 115.9 (dd, $J_{CF}$=26.4, 2.9 Hz); IR (film) cm$^{-1}$ 3211, 1707, 1640, 1474, 1456, 1386, 1261, 1247, 1198, 1183, 861, 772; LRMS (ESI): Mass calcd for [M+H]$^+$ C$_{16}$H$_{11}$F$_2$N$_2$O: 285.1. found 285.2.

Example 4

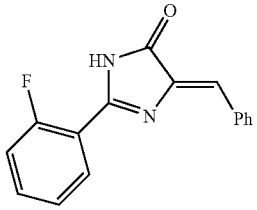 [SMILES: O=C1NC(c2ccccc2F)=N/C1=C\c1ccccc1]

(Z)-4-benzylidene-2-(2-fluorophenyl)-1H-imidazol-5 (4H)-one (4h)

Prepared according to Method A using 2-(2-fluorobenzamido)acetic acid (2.96 g, 15.0 mmol) and benzaldehyde. The crude solid was recrystallized with hot ethanol to afford imidazolidinone 1 h as a bright yellow solid (0.98 g, 24%). Analytical data for 4 h: $^1$H NMR (500 MHz, d$_6$-DMSO) δ 11.81 (br s, 1H), 8.34-8.28 (m, 2H), 8.14-8.07 (m, 1H), 7.74-7.66 (m, 1H), 7.53-7.40 (m, 5H), 7.10 (s, 1H); $^{13}$C NMR (DMSO, 126 MHz) δ 171.5, 160.3 (d, $J_{CF}$=255.8 Hz), 157.6, 139.6, 134.3 (d, $J_{CF}$=8.5 Hz), 134.1, 132.1, 130.2, 130.1, 128.7, 126.0, 125.0 (d, $J_{CF}$=3.5 Hz), 116.8 (d, $J_{CF}$=21.1 Hz), 116.5 (d, $J_{CF}$=10.6 Hz); IR (film) cm$^{-1}$ 3204, 1711, 1643, 1611, 1525, 1447, 1263, 1220, 1196, 926, 776; LRMS (ESI): Mass calcd for [M+H]$^+$ C$_{16}$H$_{12}$FN$_2$O: 267.1. found 267.3.

Example 5

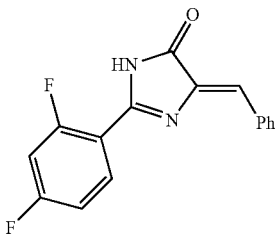 [SMILES: O=C1NC(c2ccc(F)cc2F)=N/C1=C\c1ccccc1]

(Z)-4-benzylidene-2-(2,4-difluorophenyl)-1H-imidazol-5(4H)-one (4i)

Prepared according to Method A using 2-(2,4-difluorobenzamido)acetic acid (2.60 g, 12.1 mmol) and benzaldehyde. The crude solid was recrystallized with hot ethanol to afford imidazolidinone 4i as a bright yellow solid (0.47 g, 14%). Analytical data 1i: $^1$H NMR (500 MHz, DMSO) δ 11.83 (br s, 1H), 8.32-8.27 (m, 2H), 8.17 (ap td, J=8.7, 6.5 Hz, 1H), 7.55 (ddd, J=11.6, 9.3, 2.5 Hz, 1H), 7.51-7.41 (m, 3H), 7.35 (ap td, J=8.5, 2.5 Hz, 1H), 7.09 (s, 1H); $^{13}$C NMR (DMSO, 126 MHz) δ 171.6, 164.6 (dd, $J_{CF}$=253.2, 12.5 Hz), 161.1 (dd, $J_{CF}$=258.7, 12.9 Hz), 157.0 (d, $J_{CF}$=3.8 Hz), 139.6, 134.2, 132.2, 132.0 (dd, $J_{CF}$=10.5, 3.2 Hz), 130.3, 128.8, 126.1, 113.6 (dd, $J_{CF}$=10.5, 3.6 Hz), 112.8 (dd, $J_{CF}$=22.2, 3.5 Hz), 105.5 (t, $J_{CF}$=25.9 Hz); IR (film) cm$^{-1}$ 3208, 1705, 1640, 1442, 1405, 1264, 1125, 1095; LRMS (ESI): Mass calcd for [M+H]$^+$ C$_{16}$H$_{11}$F$_2$N$_2$O: 285.1. found 285.2.

Example 6

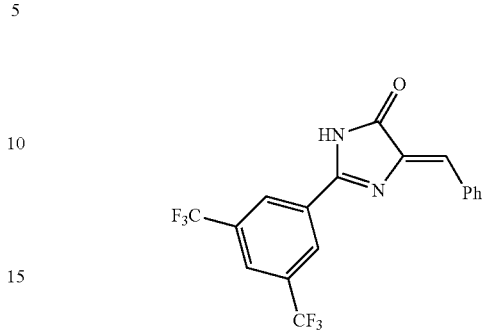

(Z)-4-benzylidene-2-(3,5-bis(trifluoromethyl)phenyl)-1H-imidazol-5(4H)-one

Prepared according to Method A using 2-(3,5-di-trifluoromethylbenzamido)acetic acid (1.58 g, 5.0 mmol) and benzaldehyde. The crude solid was recrystallized with hot ethanol to afford the imidazolidinone as a bright yellow solid (0.4 g, 21%). Analytical data: $^1$H NMR (500 MHz, d$_6$-DMSO) δ 12.41 (br s, 1H), 8.76 (s, 2H), 8.43 (s, 1H), 8.32 (ap d, J=7.0 Hz, 2H), 7.56-7.46 (m, 3H), 7.17 (s, 1H); $^{13}$C NMR (DMSO, 126 MHz) δ 171.5, 158.6, 139.8, 133.9, 132.3, 131.0 (q, $J_{CF}$=33.4 Hz), 130.5, 128.8, 127.7, 127.6, 127.3, 125.5, 122.9 (q, $J_{CF}$=273.0 Hz); IR (film) cm$^{-1}$ 1738, 1711, 1505, 1484, 1452, 1427, 1300, 1188, 1127; LRMS (ESI): Mass calcd for [M+H]$^+$ C$_{18}$H$_{11}$F$_6$N$_2$O: 385.1. found 385.2.

Example 7

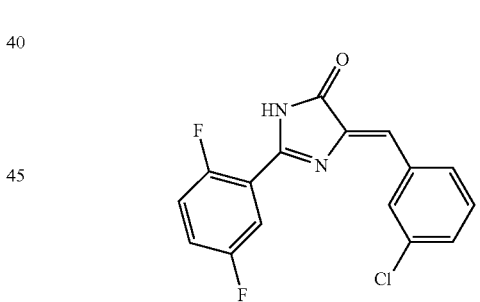

(Z)-2-(2,5-difluorophenyl)-4-(3-chlorobenzylidene)-1H-imidazol-5(4H)-one

Prepared according to Method A using 2-(2,5-difluorobenzamido)acetic acid (1.08 g, 5.0 mmol) and 3-chlorobenzaldehyde. The crude solid was recrystallized with hot ethanol to afford the imidazolidinone as a bright yellow solid (0.49 g, 31%). Analytical data: $^1$H NMR (500 MHz, DMSO) δ 11.95 (br s, 1H), 8.45 (s, 1H), 8.23 (ap d, J=8.1 Hz, 1H), 7.88 (ddd, J=8.8, 5.6, 3.1 Hz, 1H), 7.67-7.44 (m, 4H), 7.13 (s, 1H); $^{13}$C NMR (DMSO, 126 MHz) δ 171.3, 157.9 (d, $J_{CF}$=241.8 Hz), 157.7, 156.8 (d, $J_{CF}$=254.0 Hz), 140.5, 136.1, 133.4, 131.3, 130.8, 130.6, 129.9, 124.8, 121.10 (dd, $J_{CF}$=24.5, 9.1 Hz), 119.00 (dd, $J_{CF}$=24.3, 8.5 Hz), 117.66 (dd, $J_{CF}$=12.5, 8.5 Hz), 116.12 (d, $J_{CF}$=26.3 Hz); IR (film) cm$^{-1}$ 3227, 1705, 1643, 1622, 1475, 1455, 1386, 1246, 1097, 812, 785, 770; LRMS (ESI): Mass calcd for [M+H]+ C$_{16}$H$_{10}$ClF$_2$N$_2$O: 319.0. found 319.2.

Example 8

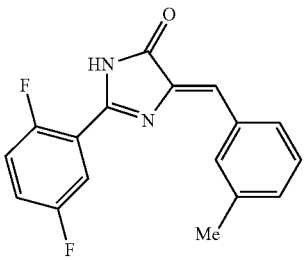 [SMILES: Cc1cccc(/C=C2\N=C(c3cc(F)ccc3F)NC2=O)c1]

(Z)-2-(2,5-difluorophenyl)-4-(3-methylbenzylidene)-1H-imidazol-5(4H)-one

Prepared according to Method A using 2-(2,5-difluorobenzamido)acetic acid (1.08 g, 5.0 mmol) and 3-methylbenzaldehyde. The crude solid was recrystallized with hot ethanol to afford the imidazolidinone as a bright yellow solid (0.39 g, 26%). Analytical data: $^1$H NMR (500 MHz, DMSO) δ 11.72 (br s, 1H), 8.15 (ap d, J=7.8 Hz, 1H), 8.07 (s, 1H), 7.88 (ddd, J=8.8, 5.6, 3.0 Hz, 1H), 7.61-7.48 (m, 2H), 7.38 (ap t, J=7.6 Hz, 1H), 7.27 (ap d, J=7.5 Hz, 1H), 7.08 (s, 1H), 2.36 (s, 3H); $^{13}$C NMR (DMSO, 126 MHz) δ 171.4, 157.9 (d, J$_{CF}$=241.3 Hz), 156.6 (d, J$_{CF}$=252.3 Hz), 156.4, 139.3, 137.8, 133.9, 132.8, 131.2, 129.4, 128.7, 127.0, 120.8 (dd, J$_{CF}$=24.3, 9.0 Hz), 118.9 (dd, J$_{CF}$=24.3, 8.8 Hz), 117.8 (dd, J$_{CF}$=12.9, 8.6 Hz), 116.0 (dd, J$_{CF}$=26.3, 2.5 Hz), 20.9; IR (film) cm$^{-1}$ 3220, 1702, 1643, 1620, 1474, 1455, 1386, 1180, 889, 877, 810; LRMS (ESI): Mass calcd for [M+H]+ C$_{17}$H$_{13}$F$_2$N$_2$O: 299.1. found 299.2.

Example 9

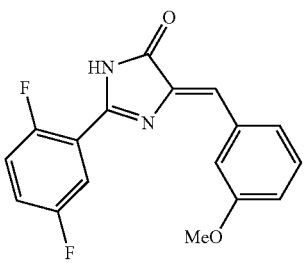 [SMILES: COc1cccc(/C=C2\N=C(c3cc(F)ccc3F)NC2=O)c1]

(Z)-2-(2,5-difluorophenyl)-4-(3-methoxybenzylidene)-1H-imidazol-5(4H)-one

Prepared according to Method A using 2-(2,5-difluorobenzamido)acetic acid (1.5 g, 7.0 mmol) and 3-methoxybenzaldehyde. The crude solid was recrystallized with hot ethanol to afford the imidazolidinone as a bright yellow solid (0.44 g, 20%). Analytical data: $^1$H NMR (500 MHz, CDCl$_3$) δ 9.06 (d, J=6.7 Hz, 1H), 8.11 (ddd, J=8.8, 5.7, 3.1 Hz, 1H), 7.96 (br s, 1H), 7.73 (ap d, J=7.6 Hz, 1H), 7.38 (ap t, J=7.9 Hz, 1H), 7.29-7.17 (m, 3H), 7.01 (dd, J=8.2, 2.6 Hz, 1H), 3.91 (s, 3H); $^{13}$C NMR (CDCl$_3$, 126 MHz) δ 171.2, 159.7, 158.9 (d, J$_{CF}$=244.6 Hz), 157.3 (dd, J$_{CF}$=247.4, 2.4 Hz), 154.1 (t, J$_{CF}$=2.9 Hz), 138.1, 135.2, 129.7, 125.7, 121.0 (dd, J$_{CF}$=24.7, 9.7 Hz), 118.1 (dd, J$_{CF}$=26.0, 8.4 Hz), 117.4, 117.2 (dd, J$_{CF}$=11.8, 8.6 Hz), 116.8, 115.8 (dd, J$_{CF}$=26.5, 2.8 Hz), 55.3; IR (film) cm$^{-1}$ 3213, 1639, 1622, 1477, 1457, 1387, 1271, 1180, 887, 770; LRMS (ESI): Mass calcd for [M+H]+ C$_{17}$H$_{13}$P$_2$N$_2$O$_2$: 315.1. found 315.3.

Example 10

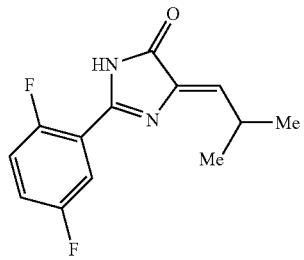 [SMILES: CC(C)/C=C1\N=C(c2cc(F)ccc2F)NC1=O]

(Z)-2-(2,5-difluorophenyl)-4-(2-methylpropylidene)-1H-imidazol-5(4H)-one

Prepared according to Method B using 2,5-difluorobenzonitrile and iso-butyraldehyde (7.82 mmol, 0.71 mL). The crude solid was recrystallized with hot ethanol to afford the imidazolidinone as a light brown solid (0.32 g, 16%). Analytical data: $^1$H NMR (500 MHz, CDCl$_3$) δ 8.79 (br s, 1H), 8.03 (ddd, J=8.7, 5.7, 3.2 Hz, 1H), 7.25-7.13 (m, 2H), 6.54 (d, J=10.1 Hz, 1H), 3.44-3.34 (m, 1H), 1.18 (d, J=6.7 Hz, 6H); $^{13}$C NMR (CDCl$_3$, 126 MHz) δ 170.1, 158.9 (d, J$_{CF}$=245.0 Hz), 157.1 (dd, J$_{CF}$=246.7, 2.4 Hz), 152.9, 144.1, 138.7, 120.7 (dd, J$_{CF}$=24.7, 9.8 Hz), 117.9 (dd, J$_{CF}$=26.0, 8.3 Hz), 117.4 (dd, J$_{CF}$=11.9, 8.5 Hz), 115.8 (dd, J$_{CF}$=26.4, 3.1 Hz), 27.9, 22.1; IR (film) cm$^{-1}$ 3227, 1709, 1664, 1485, 1474, 1456, 1388, 1297, 1247, 891, 874, 769; LRMS (ESI): Mass calcd for [M+H]+ C$_{13}$H$_{13}$F$_2$N$_2$O: 251.1 found 251.2.

Example 11

General Procedure for Reaction of Imidazolidinones with α,β-Unsaturated Aldehydes Into an oven-dried, screw-capped 1 dram vial equipped with a magnetic stirbar was weighed imidazolidinone (0.300 mmol, 1 equiv). The vial was taken into a nitrogen-filled drybox at which time azolium salt C (0.045 mmol, 0.15 equiv) and tetrabutylammonium acetate (0.090 mmol, 0.30 equiv) were added. The vial was capped with a septum cap, removed from the drybox and put under positive N$_2$ pressure. Into the vial were then successively added THF (2.0 mL, 0.15 M), the cinnamaldehyde-derived enal (0.81 mmol, 2.0 equiv), and acetic acid (0.300 mmol, 1.0 equiv) via a syringe. The reaction was stirred at room temperature until consumption of the imidazolidinone was observed by uPLCMS or for 72 h (most reactions were complete within 24 h). The reaction mixture was filtered over a pad of silica gel washing with dichloromethane and concentrated under reduced pressure. Purification by flash chromatography with EtOAc/hexanes afforded the corresponding lactones. The corresponding racemic compounds were prepared by employing the same protocol but with 2-mesityl-6,7-dihydro-5H-pyrrolo[2,1-c][1,2,4]triazol-2-ium tetrafluoroborate (0.045 mmol, 0.15 equiv, azolium A) as the catalyst.

Example 12

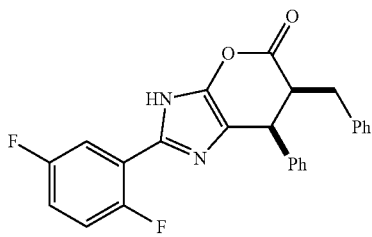 [SMILES: O=C1Oc2[nH]c(-c3cc(F)ccc3F)nc2[C@H](c2ccccc2)[C@@H]1Cc1ccccc1]

6-benzyl-2-(2,5-difluorophenyl)-7-phenyl-6,7-dihydropyrano[2,3-d]imidazol-5(3H)-one (5j)

Prepared according to the general procedure using (Z)-4-benzylidene-2-(2,5-difluorophenyl)-1H-imidazol-5(4H)-one and trans-cinnamaldehyde. The unpurified residue was purified by flash chromatography using 15% EtOAc/hexanes to afford 5j as a white solid (91 mg, 73%). Analytical data for 5j: $^1$H NMR (500 MHz, CDCl$_3$) δ 9.41 (br s, 1H), 7.91 (ddd, J=9.2, 6.1, 3.2 Hz, 1H), 7.40-7.32 (m, 5H), 7.31-7.27 (m, 1H), 7.14-7.10 (m, 2H), 7.10-7.05 (m, 1H), 7.04-6.96 (m, 3H), 4.11 (d, J=6.8 Hz, 1H), 3.64 (ddd, J=10.2, 6.8, 4.6 Hz, 1H), 3.39 (dd, J=14.9, 4.5 Hz, 1H), 2.46 (dd, J=14.9, 10.2 Hz, 1H); $^{13}$C NMR (CDCl$_3$, 126 MHz) δ 168.9, 159.1 (d, $J_{CF}$=243.1 Hz), 155.4 (d, $J_{CF}$=241.8 Hz), 148.9, 137.9, 137.0, 136.3, 129.2, 129.0, 128.6, 128.3, 128.0, 126.8, 118.4 (dd, $J_{CF}$=12.5, 9.1 Hz), 117.1 (dd, $J_{CF}$=25.7, 8.7 Hz), 116.6 (dd, $J_{CF}$=24.8, 9.4 Hz), 114.5 (dd, $J_{CF}$=27.0, 3.9 Hz), 111.0 (d, $J_{CF}$=3.8 Hz), 47.3, 38.4, 32.7; IR (film) cm$^{-1}$ 1773, 1636, 1529, 1481, 1463, 1453, 1240, 1172, 1117, 1070, 766, 731; LRMS (ESI): Mass calcd for [M+H]$^+$ C$_{25}$H$_{19}$F$_2$N$_2$O$_2$: 417.1. found 417.4; Enantiomeric ratio was measured by chiral phase HPLC (Chiralcel OD-H; 20% IPA/hexanes; 1.0 mL/min, 280 nm), Rt$_1$ (minor)=11.3, Rt$_2$ (major)=17.8 min; er=98:2.

Example 13

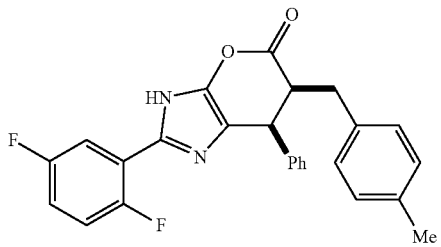 [SMILES: Cc1ccc(C[C@@H]2C(=O)Oc3[nH]c(-c4cc(F)ccc4F)nc3[C@@H]2c2ccccc2)cc1]

2-(2,5-difluorophenyl)-6-(4-methylbenzyl)-7-phenyl-6,7-dihydropyrano[2,3-d]imidazol-5(3H)-one (7)

Prepared according to the general procedure using (Z)-4-benzylidene-2-(2,5-difluorophenyl)-1H-imidazol-5(4H)-one and (E)-3-(p-tolyl)acrylaldehyde. The unpurified residue was purified by flash chromatography using 15% EtOAc/hexanes to afford 7 as an off-white solid (106 mg, 82%). Analytical data for 7: $^1$H NMR (500 MHz, CDCl$_3$) δ 9.35 (d, J=8.1 Hz, 1H), 7.89 (ddd, J=9.2, 6.1, 3.2 Hz, 1H), 7.38-7.29 (m, 3H), 7.13 (d, J=7.7 Hz, 2H), 7.05 (ddd, J=11.4, 8.9, 4.1 Hz, 1H), 7.02-6.94 (m, 5H), 4.08 (d, J=6.8 Hz, 1H), 3.58 (ddd, J=10.2, 6.8, 4.5 Hz, 1H), 3.32 (dd, J=14.8, 4.5 Hz, 1H), 2.39 (dd, J=14.9, 10.2 Hz, 1H), 2.35 (s, 3H); $^{13}$C NMR (CDCl$_3$, 126 MHz) δ 169.0, 159.1 (d, $J_{CF}$=243.8 Hz), 155.4 (d, $J_{CF}$=240.9 Hz), 148.9, 137.1, 136.34, 136.30, 134.7, 129.3, 129.2, 128.9, 128.3, 128.0, 118.4 (dd, $J_{CF}$=12.8, 9.1 Hz), 117.1 (dd, $J_{CF}$=25.7, 8.8 Hz), 116.5 (dd, $J_{CF}$=24.7, 9.6 Hz), 114.5 (dd, $J_{CF}$=26.8, 3.7 Hz), 111.1 (d, $J_{CF}$=4.0 Hz), 47.4, 38.3, 32.2, 21.1; IR (film) cm$^{-1}$ 3029, 2923, 1768, 1618, 1529, 1482, 1463, 1452, 1351, 1240, 1172, 1118, 1102, 811, 766, 736, 700; LRMS (ESI): Mass calcd for [M+H]$^+$ C$_{26}$H$_{21}$F$_2$N$_2$O$_2$: 431.2. found 431.4; Enantiomeric ratio was measured by chiral phase HPLC (Chiralcel OD-H; 4% IPA/2% MeOH/hexanes; 0.7 mL/min, 280 nm), Rt$_1$ (major)=34.4, Rt$_2$ (minor)=43.7 min; er=99:1.

Example 14

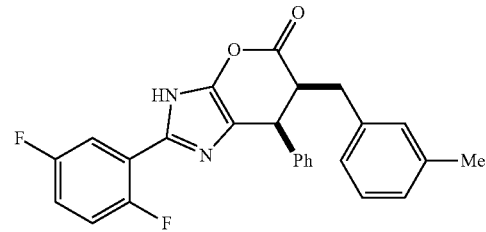 [SMILES: Cc1cccc(C[C@@H]2C(=O)Oc3[nH]c(-c4cc(F)ccc4F)nc3[C@@H]2c2ccccc2)c1]

2-(2,5-difluorophenyl)-6-(3-methylbenzyl)-7-phenyl-6,7-dihydropyrano[2,3-d]imidazol-5(3H)-one (8)

Prepared according to the general procedure using (Z)-4-benzylidene-2-(2,5-difluorophenyl)-1H-imidazol-5(4H)-one and (E)-3-(m-tolyl)acrylaldehyde. The unpurified residue was purified by flash chromatography using 15% EtOAc/hexanes to afford 8 as an off-white solid (78 mg, 61%). Analytical data for 8: $^1$H NMR (500 MHz, CDCl$_3$) δ 9.39 (d, J=7.3 Hz, 1H), 7.88 (ddd, J=9.2, 6.1, 3.2 Hz, 1H), 7.37-7.29 (m, 3H), 7.20-7.12 (m, 3H), 7.11-7.01 (m, 2H), 6.97 (ddd, J=6.2, 4.9, 1.9 Hz, 3H), 4.18 (d, J=6.9 Hz, 1H), 3.62 (ddd, J=9.7, 6.9, 4.8 Hz, 1H), 3.27 (dd, J=15.3, 4.8 Hz, 1H), 2.53 (dd, J=15.3, 9.8 Hz, 1H), 2.04 (s, 3H); $^{13}$C NMR (CDCl$_3$, 126 MHz) δ 169.1, 159.1 (d, $J_{CF}$=243.5 Hz), 155.4 (dd, $J_{CF}$=241.0, 2.4 Hz), 148.8, 137.2, 136.7, 136.4, 135.9, 130.7, 129.3, 128.7, 128.3, 127.9, 126.7, 126.0, 118.4 (dd, $J_{CF}$=12.8, 8.9 Hz), 117.1 (dd, $J_{CF}$=25.8, 8.6 Hz), 116.6 (dd, $J_{CF}$=24.8, 9.5 Hz), 114.5 (dd, $J_{CF}$=26.8, 3.8 Hz), 110.9 (d, $J_{CF}$=3.8 Hz), 45.6, 38.5, 29.5, 19.4; IR (film) cm$^{-1}$ 11773, 1636, 1618, 1529, 1481, 1463, 1452, 1411, 1240, 1171, 1122, 1100, 1078, 766, 747, 700; LRMS (ESI): Mass calcd for [M+H]$^+$ C$_{26}$H$_{21}$F$_2$N$_2$O$_2$: 431.2. found 431.4; Enantiomeric ratio was measured by chiral phase HPLC (Chiralcel OD-H; 4% IPA/2% MeOH/hexanes; 0.7 mL/min, 280 nm), Rt$_1$ (minor)=39.1, Rt$_2$ (major)=69.4 min; er=97:3.

Example 15

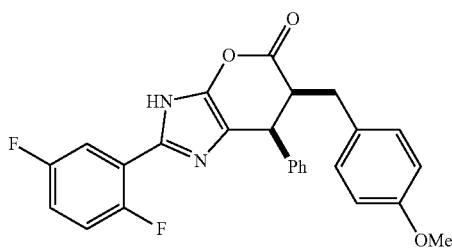 [SMILES: COc1ccc(C[C@@H]2C(=O)Oc3[nH]c(-c4cc(F)ccc4F)nc3[C@@H]2c2ccccc2)cc1]

2-(2,5-difluorophenyl)-6-(4-methoxybenzyl)-7-phenyl-6,7-dihydropyrano[2,3-d]imidazol-5(3H)-one (9)

Prepared according to the general procedure using (Z)-4-benzylidene-2-(2,5-difluorophenyl)-1H-imidazol-5(4H)-one and (E)-3-(4-methoxyphenyl)acrylaldehyde. The unpurified residue was purified by flash chromatography using 15% EtOAc/hexanes to afford 9 as an off-white solid (102 mg, 76%). Analytical data for 9: $^1$H NMR (500 MHz, CDCl$_3$) δ 9.38 (d, J=8.1 Hz, 1H), 7.89 (ddd, J=9.2, 6.1, 3.2 Hz, 1H), 7.39-7.29 (m, 3H), 7.10-6.93 (m, 6H), 6.88-6.83 (m, 2H), 4.09 (d, J=6.8 Hz, 1H), 3.81 (s, 3H), 3.55 (ddd, J=10.1, 6.8, 4.6 Hz, 1H), 3.29 (dd, J=14.9, 4.6 Hz, 1H), 2.38 (dd, J=14.9, 10.1 Hz, 1H); $^{13}$C NMR (CDCl$_3$, 126 MHz) δ 169.0, 159.1 (d, $J_{CF}$=243.6 Hz), 158.4, 155.4 (d, $J_{CF}$=241.1 Hz), 148.9, 137.1, 136.3, 130.0, 129.7, 129.2, 128.3, 128.0, 118.4 (dd, $J_{CF}$=12.3, 9.5 Hz), 117.1 (dd, $J_{CF}$=25.7, 8.7 Hz), 116.5 (dd, $J_{CF}$=24.7, 9.5 Hz), 114.0, 114.5 (dd, $J_{CF}$=26.8, 3.7 Hz), 111.0 (d, $J_{CF}$=3.8 Hz), 55.3, 47.5, 38.3, 31.8; IR (film) cm$^{-1}$ 1772, 1617, 1528, 1513, 1481, 1464 1249, 1176, 1118, 1100, 1033, 766, 735, 700; LRMS (ESI): Mass calcd for [M+H]$^+$ C$_{26}$H$_{21}$F$_2$N$_2$O$_3$: 447.1. found 447.4; Enantiomeric ratio was measured by chiral phase HPLC (Chiralcel OD-H; 5% IPA/3% MeOH/hexanes 0.5 mL/min, 280 nm), Rt$_1$ (major)=48.1, Rt$_2$ (minor)=56.9 min; er=99:1.

Example 16

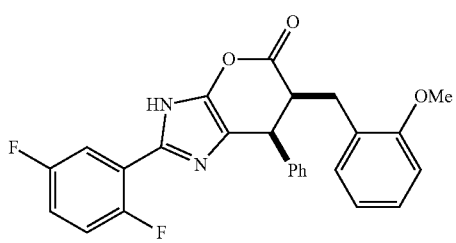 [SMILES: COc1ccccc1C[C@@H]1C(=O)Oc2[nH]c(-c3cc(F)ccc3F)nc2[C@@H]1c1ccccc1]

2-(2,5-difluorophenyl)-6-(2-methoxybenzyl)-7-phenyl-6,7-dihydropyrano[2,3-d]imidazol-5(3H)-one (10)

Prepared according to the general procedure using (Z)-4-benzylidene-2-(2,5-difluorophenyl)-1H-imidazol-5(4H)-one and (E)-3-(2-methoxyphenyl)acrylaldehyde. The unpurified residue was purified by flash chromatography using 15% EtOAc/hexanes to afford 10 as an off-white solid (81 mg, 61%). Analytical data for 10: $^1$H NMR (500 MHz, CDCl$_3$) δ 9.34 (d, J=8.1 Hz, 1H), 7.89 (ddd, J=9.2, 6.0, 3.2 Hz, 1H), 7.38-7.29 (m, 3H), 7.27-7.21 (m, 1H), 7.09-7.00 (m, 3H), 7.00-6.92 (m, 1H), 6.91 (dd, J=7.6, 1.8 Hz, 1H), 6.86 (ap t, J=7.5 Hz, 2H), 4.06 (d, J=6.9 Hz, 1H), 3.84 (ddd, J=8.9, 6.9, 5.2 Hz, 1H), 3.80 (s, 3H), 3.26 (dd, J=14.2, 5.2 Hz, 1H), 2.49 (dd, J=14.2, 8.8 Hz, 1H); $^{13}$C NMR (CDCl$_3$, 126 MHz) δ 169.4, 159.1 (d, $J_{CF}$=243.7 Hz), 157.8, 155.3 (d, $J_{CF}$=240.5 Hz), 148.9, 137.6, 136.1, 131.9, 129.1, 128.1, 128.0, 126.0, 120.2, 117.1 (dd, $J_{CF}$=25.8, 8.7 Hz), 116.4 (dd, $J_{CF}$=24.7, 9.4 Hz), 114.5 (dd, $J_{CF}$=27.5, 3.0 Hz), 111.3 (d, $J_{CF}$=2.9 Hz), 110.1, 55.2, 44.8, 39.0, 29.1; IR (film) cm$^{-1}$ 1773, 1637, 1482, 1464, 1243, 1173, 1122, 1101, 1030, 813, 765, 738, 700; LRMS (ESI): Mass calcd for [M+H]$^+$ C$_{26}$H$_{21}$F$_2$N$_2$O$_3$: 447.1. found 447.4; Enantiomeric ratio was measured by chiral phase HPLC (Chiralcel OD-H; 5% IPA/3% MeOH/hexanes 0.5 mL/min, 280 nm), Rt$_1$ (minor)=32.2, Rt$_2$ (major)=42.5 min; er=96:4.

Example 17

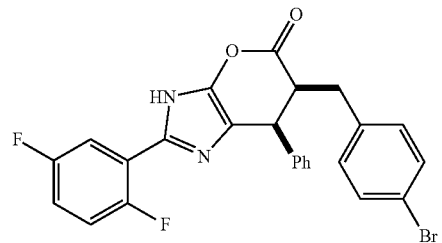 [SMILES: O=C1Oc2[nH]c(-c3cc(F)ccc3F)nc2[C@H](c2ccccc2)[C@@H]1Cc1ccc(Br)cc1]

6-(4-bromobenzyl)-2-(2,5-difluorophenyl)-7-phenyl-6,7-dihydropyrano[2,3-d]imidazol-5(3H)-one (11)

Prepared according to the general procedure using (Z)-4-benzylidene-2-(2,5-difluorophenyl)-1H-imidazol-5(4H)-one and (E)-3-(4-bromophenyl)acrylaldehyde. The unpurified residue was purified by flash chromatography using 15% EtOAc/hexanes to afford 11 as a white solid (95 mg, 64%). Analytical data for 11: $^1$H NMR (500 MHz, CDCl$_3$) δ 9.37 (d, J=8.0 Hz, 1H), 7.89 (ddd, J=9.1, 6.1, 3.2 Hz, 1H), 7.47-7.41 (m, 2H), 7.39-7.30 (m, 3H), 7.09-7.02 (m, 1H), 7.02-6.92 (m, 5H), 4.08 (d, J=6.9 Hz, 1H), 3.56 (ddd, J=9.8, 6.8, 5.0 Hz, 1H), 3.27 (dd, J=14.9, 4.9 Hz, 1H), 2.41 (dd, J=14.9, 9.9 Hz, 1H); $^{13}$C NMR (CDCl$_3$, 126 MHz) δ 168.6, 159.1 (d, $J_{CF}$=243.6 Hz), 155.4 (d, $J_{CF}$=240.8 Hz), 148.9, 136.9, 136.8, 136.5, 131.7, 130.8, 129.3, 128.4, 127.9, 120.6, 118.3 (dd, $J_{CF}$=12.4, 9.4 Hz), 117.1 (dd, $J_{CF}$=25.7, 8.3 Hz), 116.6 (dd, $J_{CF}$=24.5, 9.6 Hz), 114.5 (dd, $J_{CF}$=26.9, 3.8 Hz), 110.7 (d, $J_{CF}$=3.7 Hz), 47.1, 38.5, 32.3; IR (film) cm$^{-1}$ 1773, 1618, 1529, 1481, 1463, 1240, 1171, 1119, 1099, 1071, 1011, 765, 740, 699; LRMS (ESI): Mass calcd for [M+H]$^+$ C$_{25}$H$_{18}$BrF$_2$N$_2$O$_2$: 495.0. found 495.0; Enantiomeric ratio was measured by chiral phase HPLC (Chiralcel OD-H; 10% IPA/hexanes; 1.0 mL/min, 280 nm), Rt$_1$ (major)=33.1, Rt$_2$ (minor)=52.8 min; er=96:4.

Example 18

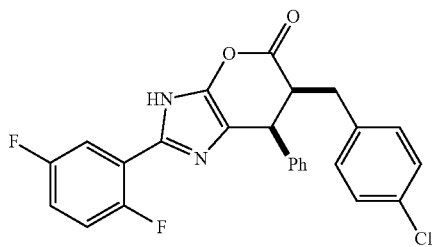 [SMILES: O=C1Oc2[nH]c(-c3cc(F)ccc3F)nc2[C@H](c2ccccc2)[C@@H]1Cc1ccc(Cl)cc1]

6-(4-chlorobenzyl)-2-(2,5-difluorophenyl)-7-phenyl-6,7-dihydropyrano[2,3-d]imidazol-5(3H)-one (12)

Prepared according to the general procedure using (Z)-4-benzylidene-2-(2,5-difluorophenyl)-1H-imidazol-5(4H)-one and (E)-3-(4-chlorophenyl)acrylaldehyde. The unpurified residue was purified by flash chromatography using 15% EtOAc/hexanes to afford 12 as a white solid (78 mg, 58%). Analytical data for 12: $^1$H NMR (500 MHz, CDCl$_3$) δ 9.37 (d, J=7.9 Hz, 1H), 7.89 (ddd, J=9.2, 6.1, 3.2 Hz, 1H), 7.38-7.31 (m, 2H), 7.31-7.26 (m, 3H), 7.12-6.92 (m, 6H), 4.08 (d, J=6.8 Hz, 1H), 3.56 (ddd, J=9.8, 6.9, 4.9 Hz, 1H), 3.29 (dd, J=14.9, 5.0 Hz, 1H), 2.43 (dd, J=14.9, 9.8 Hz, 1H); $^{13}$C NMR (CDCl$_3$, 126 MHz) δ 168.7, 159.11 (d, $J_{CF}$=244.0 Hz), 155.38 (d, $J_{CF}$=242.2 Hz), 148.9, 136.8, 136.5, 136.3, 132.6, 130.4, 129.3, 128.8, 128.4, 127.9, 118.32 (dd, $J_{CF}$=12.4, 9.3 Hz), 117.12 (dd, $J_{CF}$=25.5, 8.6 Hz), 116.64 (dd, $J_{CF}$=24.8, 9.2 Hz), 114.51 (dd, $J_{CF}$=26.9, 3.7 Hz), 110.69 (d, $J_{CF}$=3.8 Hz), 47.2, 38.6, 32.3; IR (film) cm$^{-1}$ 1769, 1638, 1492, 1481, 1462, 1239, 1171, 1118, 1096, 1032, 813, 766, 741, 699; LRMS (ESI): Mass calcd for [M+H]$^+$ C$_{25}$H$_{18}$ClF$_2$N$_2$O$_2$: 451.1. found 451.3; Enantiomeric ratio was measured by chiral phase HPLC (Chiralcel OD-H; 5% IPA/3% MeOH/hexanes 0.5 mL/min, 280 nm), Rt$_1$ (major)=40.5, Rt$_2$ (minor)=50.6 min; er=98:2.

Example 19

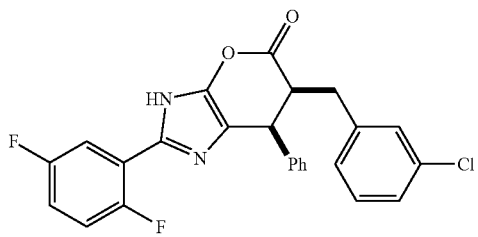 [SMILES: O=C1Oc2[nH]c(-c3cc(F)ccc3F)nc2[C@H](c2ccccc2)[C@@H]1Cc1cccc(Cl)c1]

6-(3-chlorobenzyl)-2-(2,5-difluorophenyl)-7-phenyl-6,7-dihydropyrano[2,3-d]imidazol-5(3H)-one (13)

Prepared according to the general procedure using (Z)-4-benzylidene-2-(2,5-difluorophenyl)-1H-imidazol-5(4H)-one and (E)-3-(3-chlorophenyl)acrylaldehyde. The unpurified residue was purified by flash chromatography using 15% EtOAc/hexanes to afford 13 as a white solid (62 mg, 46%). Analytical data for 13: $^1$H NMR (500 MHz, CDCl$_3$) δ 9.41 (s, 1H), 7.88 (ddd, J=9.1, 6.0, 3.2 Hz, 1H), 7.40-7.29 (m, 3H), 7.31-7.22 (m, 2H), 7.10-7.02 (m, 2H), 7.02-6.93 (m, 4H), 4.09 (d, J=6.8 Hz, 1H), 3.58 (ddd, J=9.8, 6.9, 4.9 Hz, 1H), 3.31 (dd, J=14.9, 4.9 Hz, 1H), 2.42 (dd, J=14.9, 9.8 Hz, 1H); $^{13}$C NMR (CDCl$_3$, 126 MHz) δ 168.6, 159.1 (d, $J_{CF}$=243.4 Hz), 155.4 (d, $J_{CF}$=241.8 Hz), 148.9, 140.0, 136.8, 136.5, 134.4, 129.9, 129.3, 129.1, 128.5, 127.9, 127.3, 127.0, 118.3 (dd, $J_{CF}$=12.6, 8.9 Hz), 117.1 (dd, $J_{CF}$=25.6, 8.9 Hz), 116.6 (dd, $J_{CF}$=24.8, 9.3 Hz), 114.5 (dd, $J_{CF}$=26.8, 3.6 Hz), 110.7 (d, $J_{CF}$=3.8 Hz), 47.0, 38.6, 32.6; IR (film) cm$^{-1}$ 1773, 1636, 1597, 1528, 1481, 1464, 1171, 1117, 1079, 813, 741; LRMS (ESI): Mass calcd for [M+H]$^+$ C$_{25}$H$_{18}$ClF$_2$N$_2$O$_2$: 451.1. found 451.3; Enantiomeric ratio was measured by chiral phase HPLC (Chiralcel OD-H; 5% IPA/3% MeOH/hexanes 0.5 mL/min, 280 nm), Rt$_1$ (minor)=49.1, Rt$_2$ (major)=70.2 min; er=>99:1.

Example 20

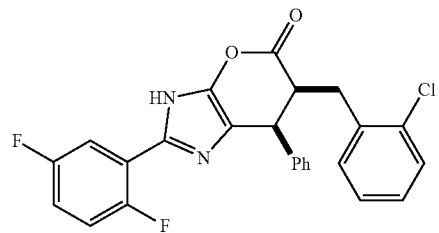 [SMILES: O=C1Oc2[nH]c(-c3cc(F)ccc3F)nc2[C@H](c2ccccc2)[C@@H]1Cc1ccccc1Cl]

6-(2-chlorobenzyl)-2-(2,5-difluorophenyl)-7-phenyl-6,7-dihydropyrano[2,3-d]imidazol-5(3H)-one (14)

Prepared according to the general procedure using (Z)-4-benzylidene-2-(2,5-difluorophenyl)-1H-imidazol-5(4H)-one and (E)-3-(2-chlorophenyl)acrylaldehyde. The unpurified residue was purified by flash chromatography using 15% EtOAc/hexanes to afford 14 as a white solid (65 mg, 48%). Analytical data for 14: $^1$H NMR (500 MHz, CDCl$_3$) δ 9.40 (d, J=8.0 Hz, 1H), 7.88 (ddd, J=9.2, 6.1, 3.2 Hz, 1H), 7.39-7.32 (m, 3H), 7.28-7.22 (m, 2H), 7.10-7.03 (m, 2H), 7.01-6.94 (m, 4H), 4.09 (d, J=6.9 Hz, 1H), 3.58 (ddd, J=9.8, 6.8, 4.9 Hz, 1H), 3.31 (dd, J=14.9, 4.9 Hz, 1H), 2.42 (dd, J=14.9, 9.8 Hz, 1H); $^{13}$C NMR (CDCl$_3$, 126 MHz) δ 168.6, 159.1 (d, $J_{CF}$=243.3 Hz), 155.4 (d, $J_{CF}$=240.2 Hz), 148.9, 140.0, 136.8, 136.5, 134.4, 129.9, 129.3, 129.1, 128.5, 127.9, 127.3, 127.0, 118.3 (dd, $J_{CF}$=13.0, 9.3 Hz), 117.1 (dd, $J_{CF}$=25.8, 8.7 Hz), 116.6 (dd, $J_{CF}$=24.8, 9.5 Hz), 114.5 (dd, $J_{CF}$=26.8, 3.7 Hz), 110.7 (d, $J_{CF}$=3.8 Hz), 47.0, 38.6, 32.6; IR (film) cm$^{-1}$ 1772, 1636, 1619, 1598, 1529, 1481, 1463, 1172, 1118, 1079, 875, 813, 766, 741, 697; LRMS (ESI): Mass calcd for [M+H]$^+$ C$_{25}$H$_{18}$ClF$_2$N$_2$O$_2$: 451.1. found 451.3; Enantiomeric ratio was measured by chiral phase HPLC (Chiralcel OD-H; 4% IPA/2% MeOH/hexanes 1.0 mL/min, 280 nm), Rt$_1$ (major)=20.7, Rt$_2$ (minor)=23.6 min; er=92:8.

Example 21

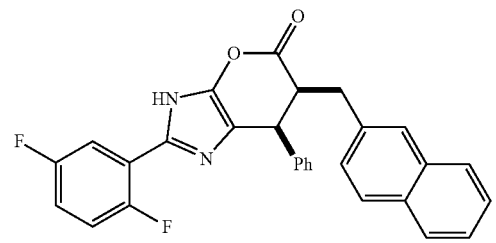 [SMILES: O=C1Oc2[nH]c(-c3cc(F)ccc3F)nc2[C@H](c2ccccc2)[C@@H]1Cc1ccc2ccccc2c1]

2-(2,5-difluorophenyl)-6-(naphthalen-2-ylmethyl)-7-phenyl-6,7-dihydropyrano[2,3-d]imidazol-5(3H)-one (15)

Prepared according to the general procedure using (Z)-4-benzylidene-2-(2,5-difluorophenyl)-1H-imidazol-5(4H)-one and (E)-3-(naphthalen-2-yl)acrylaldehyde. The unpurified residue was purified by flash chromatography using 15% EtOAc/hexanes to afford 15 as an off-white solid (99 mg, 71%). Analytical data for 15: $^1$H NMR (500 MHz, CDCl$_3$) δ 9.35 (d, J=8.3 Hz, 1H), 7.89 (ddd, J=9.2, 6.1, 3.3 Hz, 1H), 7.86-7.80 (m, 2H), 7.78-7.74 (m, 1H), 7.53-7.45 (m, 3H), 7.38-7.32 (m, 3H), 7.24 (dd, J=8.5, 1.8 Hz, 1H), 7.07-6.92 (m, 4H), 4.08 (d, J=6.8 Hz, 1H), 3.74 (ddd, J=10.4, 6.8, 4.5 Hz, 1H), 3.54 (dd, J=14.8, 4.5 Hz, 1H), 2.60 (dd, J=14.9, 10.3 Hz, 1H); $^{13}$C NMR (CDCl$_3$, 126 MHz) δ 168.9, 159.1 (d, $J_{CF}$=243.3 Hz), 155.3 (d, $J_{CF}$=241.8 Hz), 148.9, 137.1, 136.4, 135.2, 133.4, 132.3, 129.2, 128.4, 128.4, 128.1, 127.8, 127.7, 127.4, 127.0, 126.3, 125.7, 118.4 (dd, $J_{CF}$=12.5, 8.9 Hz), 117.1 (dd, $J_{CF}$=25.6, 8.7 Hz), 116.6 (dd, $J_{CF}$=24.9, 9.9 Hz), 114.5 (dd, $J_{CF}$=26.8, 3.9 Hz), 111.0 (d, $J_{CF}$=3.7 Hz), 47.1, 38.4, 32.9; IR (film) cm$^{-1}$ 3057, 3030, 1770, 1635, 1619, 1530, 1481, 1411, 1172, 1116, 1104, 1032, 814, 766, 738, 701; LRMS (ESI): Mass calcd for [M+H]$^+$ C$_{29}$H$_{21}$F$_2$N$_2$O$_2$: 467.2. found 467.4; Enantiomeric ratio was measured by chiral phase HPLC (Chiralcel AD-H; 7% IPA/hexanes 1.0 mL/min, 230 nm), Rt$_1$ (major)=37.8, Rt$_2$ (minor)=48.3 min; er=96:4.

Example 22

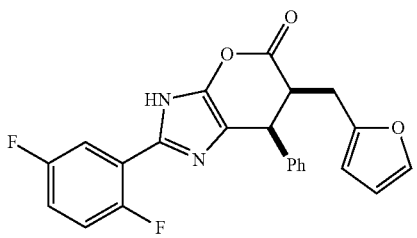 [SMILES: O=C1Oc2[nH]c(-c3cc(F)ccc3F)nc2[C@H](c2ccccc2)[C@@H]1Cc1ccco1]

2-(2,5-difluorophenyl)-6-(furan-2-ylmethyl)-7-phenyl-6,7-dihydropyrano[2,3-d]imidazol-5(3H)-one (16)

Prepared according to the general procedure using (Z)-4-benzylidene-2-(2,5-difluorophenyl)-1H-imidazol-5(4H)-one and (E)-3-(furan-2-yl)acrylaldehyde. The unpurified residue was purified by flash chromatography using 15% EtOAc/hexanes to afford 16 as an off-white solid (80 mg, 66%). Analytical data for 16: $^1$H NMR (500 MHz, CDCl$_3$) δ 9.45 (d, J=8.1 Hz, 1H), 7.90 (ddd, J=9.2, 6.1, 3.2 Hz, 1H), 7.37 (ap d, J=1.2 Hz, 1H), 7.37-7.27 (m, 3H), 7.11-7.01 (m, 3H), 7.01-6.94 (m, 1H), 6.34 (dd, J=3.2, 1.9 Hz, 1H), 6.02 (d, J=2.9 Hz, 1H), 4.20 (d, J=6.9 Hz, 1H), 3.70 (ddd, J=10.3, 6.8, 4.1 Hz, 1H), 3.30 (ddd, J=15.9, 4.2, 1.2 Hz, 1H), 2.48 (dd, J=15.8, 10.4 Hz, 1H); $^{13}$C NMR (CDCl$_3$, 126 MHz) δ 168.4, 159.1 (d, $J_{CF}$=243.8 Hz), 155.4 (dd, $J_{CF}$=241.2, 2.2 Hz), 151.8, 149.1, 141.6, 136.7, 136.5, 129.2, 128.3, 128.0, 118.4 (dd, $J_{CF}$=12.8, 9.2 Hz), 117.1 (dd, $J_{CF}$=25.6, 8.8 Hz), 116.6 (dd, $J_{CF}$=24.9, 9.6 Hz), 114.5 (dd, $J_{CF}$=26.9, 3.7 Hz), 110.7 (d, $J_{CF}$=3.9 Hz), 110.4, 107.6, 44.9, 38.5, 25.6; IR (film) cm$^{-1}$ 1770, 1636, 1620, 1529, 1482, 1464, 1452, 1173, 1117, 1008, 919, 902, 885, 875, 814, 766, 736, 700; LRMS (ESI): Mass calcd for [M+H]$^+$ C$_{23}$H$_{17}$F$_2$N$_2$O$_3$: 407.1. found 407.3; Enantiomeric ratio was measured by chiral phase HPLC (Chiralcel OD-H; 5% IPA/3% MeOH/hexanes 0.5 mL/min, 280 nm), Rt$_1$ (major)=32.4, Rt$_2$ (minor)=36.4 min; er=98:2.

Example 23

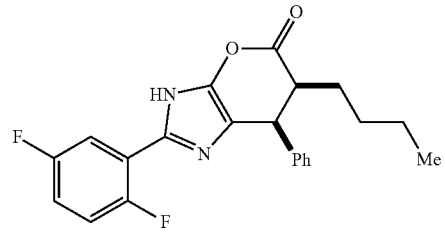 [SMILES: CCCC[C@@H]1C(=O)Oc2[nH]c(-c3cc(F)ccc3F)nc2[C@@H]1c1ccccc1]

6-butyl-2-(2,5-difluorophenyl)-7-phenyl-6,7-dihydropyrano[2,3-d]imidazol-5(3H)-one (17)

Prepared according to the general procedure using (Z)-4-benzylidene-2-(2,5-difluorophenyl)-1H-imidazol-5(4H)-one and (E)-hex-2-enal. The unpurified residue was purified by flash chromatography using 15% EtOAc/hexanes to afford 17 as an off-white solid (103 mg, 90%). Analytical data for 17: $^1$H NMR (500 MHz, CDCl$_3$) δ 9.54 (d, J=8.5 Hz, 1H), 7.88 (ddd, J=9.2, 6.1, 3.2 Hz, 1H), 7.35-7.27 (m, 2H), 7.12-7.03 (m, 3H), 7.01-6.93 (m, 1H), 4.29 (d, J=6.8 Hz, 1H), 3.18-3.08 (m, 1H), 1.86-1.73 (m, 1H), 1.46-1.36 (m, 2H), 1.36-1.15 (m, 4H), 0.86 (t, J=7.3 Hz, 3H); $^{13}$C NMR (CDCl$_3$, 126 MHz) δ 169.2, 159.1 (d, $J_{CF}$=243.5 Hz), 155.4 (d, $J_{CF}$=240.4 Hz), 149.2, 137.2, 136.3, 129.2, 128.1, 127.7, 118.5 (dd, $J_{CF}$=12.8, 9.0 Hz), 117.1 (dd, $J_{CF}$=25.6, 8.8 Hz), 116.5 (dd, $J_{CF}$=24.7, 9.4 Hz), 114.5 (dd, $J_{CF}$=27.1, 3.8 Hz), 110.6 (d, $J_{CF}$=3.8 Hz), 46.0, 39.3, 29.3, 26.7, 22.4, 13.9; IR (film) cm$^{-1}$ 3084, 3030, 2957, 1773, 1619, 1528, 1482, 1464, 1238, 1174, 1138, 1118, 1094, 1068, 874, 812, 766, 699; LRMS (ESI): Mass calcd for [M+H]$^+$ C$_{22}$H$_{21}$F$_2$N$_2$O$_2$: 383.2. found 383.4; Enantiomeric ratio was measured by chiral phase HPLC (Chiralcel OD-H; 0-30 min: isocratic 12% IPA/hexanes; 30-45 min: 20% IPA/hexanes 1.0 mL/min, 280 nm), Rt$_1$ (major)=16.8, Rt$_2$ (minor)=37.6 min; er=>99:1.

Example 24

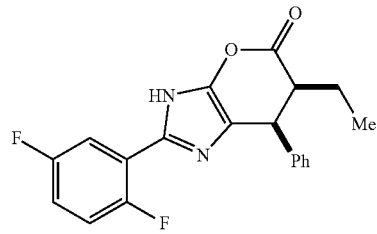 [SMILES: CC[C@@H]1C(=O)Oc2[nH]c(-c3cc(F)ccc3F)nc2[C@@H]1c1ccccc1]

2-(2,5-difluorophenyl)-6-ethyl-7-phenyl-6,7-dihydropyrano[2,3-d]imidazol-5(3H)-one (18)

Prepared according to the general procedure using (Z)-4-benzylidene-2-(2,5-difluorophenyl)-1H-imidazol-5(4H)-one and trans-crotonaldehyde. The unpurified residue was purified by flash chromatography using 15% EtOAc/hexanes to afford 18 as an off-white solid (85 mg, 80%). Analytical data for 18: $^1$H NMR (500 MHz, CDCl$_3$) δ 9.43 (br s, 1H), 7.91 (ddd, J=9.3, 6.1, 3.2 Hz, 1H), 7.37-7.28 (m, 3H), 7.15-7.03 (m, 3H), 7.02-6.93 (m, 1H), 4.31 (d, J=6.9 Hz, 1H), 3.06 (q, J=6.8 Hz, 1H), 1.89-1.78 (m, 1H), 1.31-1.20 (m, 1H), 1.04 (t, J=7.4 Hz, 3H); $^{13}$C NMR (CDCl$_3$, 126 MHz) δ 169.0, 159.1 (d, J$_{CF}$=243.5 Hz), 155.4 (d, J$_{CF}$=240.5 Hz), 149.3, 137.1, 136.4, 129.2, 128.2, 127.7, 118.5 (dd, J$_{CF}$=13.1, 9.2 Hz), 117.1 (dd, J$_{CF}$=25.7, 8.8 Hz), 116.5 (dd, J$_{CF}$=24.9, 9.5 Hz), 114.5 (dd, J$_{CF}$=27.0, 4.0 Hz), 110.5 (d, J$_{CF}$=3.9 Hz), 47.8, 39.1, 20.4, 11.9; IR (film) cm$^{-1}$ 2968, 2933, 2877, 1773, 1763, 1618, 1528, 1482, 1464, 1388, 1174, 1138, 1115, 1089, 1067, 766, 736, 699; LRMS (ESI): Mass calcd for [M+H]$^+$ C$_{20}$H$_{17}$F$_2$N$_2$O$_2$: 355.1. found 355.3; Enantiomeric ratio was measured by chiral phase HPLC (Chiralcel OD-H; 15% IPA/hexanes 1.0 mL/min, 280 nm), Rt$_1$=20.2 min (major), Rt$_2$=36.1 min (minor)); er=>99:1.

Example 25

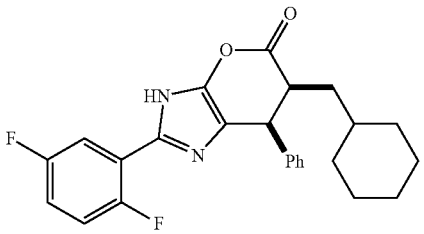 [SMILES: O=C1Oc2[nH]c(-c3cc(F)ccc3F)nc2[C@H](c2ccccc2)[C@@H]1CC1CCCCC1]

6-(cyclohexylmethyl)-2-(2,5-difluorophenyl)-7-phenyl-6,7-dihydropyrano[2,3-d]imidazol-5(3H)-one (19)

Prepared according to the general procedure using (Z)-4-benzylidene-2-(2,5-difluorophenyl)-1H-imidazol-5(4H)-one and (E)-3-cyclohexylacrylaldehyde. After 72 h, the reaction only reached 64% conversion by $^1$H NMR. The unpurified residue was purified by flash chromatography using 15% EtOAc/hexanes to afford 19 as an off-white solid (71 mg, 56%). Analytical data for 19: $^1$H NMR (500 MHz, CDCl$_3$) δ 9.45 (d, J=8.3 Hz, 1H), 7.90 (ddd, J=9.2, 6.1, 3.2 Hz, 1H), 7.36-7.27 (m, 3H), 7.13-7.04 (m, 3H), 7.01-6.93 (m, 1H), 4.24 (d, J=6.9 Hz, 1H), 3.29 (q, J=6.9 Hz, 1H), 1.74-1.61 (m, 6H), 1.49-1.40 (m, 1H), 1.29-1.18 (m, 2H), 1.18-1.04 (m, 2H), 0.91-0.81 (m, 2H); $^{13}$C NMR (CDCl$_3$, 126 MHz) δ 169.5, 159.1 (d, J$_{CF}$=243.4 Hz), 155.4 (dd, J$_{CF}$=240.8, 2.1 Hz), 149.3, 137.3, 136.3, 129.2, 128.1, 127.7, 118.5 (dd, J$_{CF}$=12.9, 9.1 Hz), 117.1 (dd, J$_{CF}$=25.7, 8.7 Hz), 116.5 (dd, J$_{CF}$=24.7, 9.5 Hz), 114.5 (dd, J$_{CF}$=27.0, 3.8 Hz), 110.6 (d, J$_{CF}$=3.9 Hz), 43.0, 39.6, 34.6, 34.4, 33.4, 32.8, 26.4, 26.2, 26.1; IR (film) cm$^{-1}$ 2923, 2851, 1770, 1637, 1619, 1529, 1481, 1463, 1450, 1387, 1172, 1115, 1094, 881, 812, 766, 737, 700; LRMS (ESI): Mass calcd for [M+H]$^+$ C$_{25}$H$_{25}$F$_2$N$_2$O$_2$: 423.2. found 423.4; Enantiomeric ratio was measured by chiral phase HPLC (Chiralcel OD-H; 15% IPA/hexanes 0.7 mL/min, 280 nm), Rt$_1$ (major)=9.1, Rt$_2$ (minor)=25.0 min; er=98:2.

Example 26

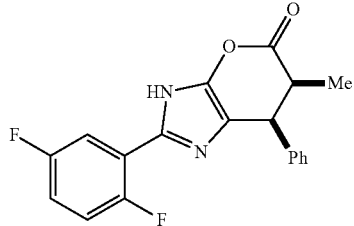 [SMILES: C[C@@H]1C(=O)Oc2[nH]c(-c3cc(F)ccc3F)nc2[C@@H]1c1ccccc1]

2-(2,5-difluorophenyl)-6-methyl-7-phenyl-6,7-dihydropyrano[2,3-d]imidazol-5(3H)-one (20)

Prepared according to the general procedure using (Z)-4-benzylidene-2-(2,5-difluorophenyl)-1H-imidazol-5(4H)-one and acrolein. After 72 h, the reaction only reached 63% conversion by $^1$H NMR. The unpurified residue was purified by flash chromatography using 15% EtOAc/hexanes to afford 20 as an off-white solid (43 mg, 42%). Analytical data for 20: $^1$H NMR (500 MHz, CDCl$_3$) δ 9.48 (br s, 1H), 7.91 (ddd, J=9.2, 6.1, 3.2 Hz, 1H), 7.37-7.27 (m, 3H), 7.12-7.03 (m, 3H), 7.02-6.95 (m, 1H), 4.21 (d, J=7.2 Hz, 1H), 3.36 (ap, J=7.0 Hz, 1H), 1.11 (d, J=6.9 Hz, 3H); $^{13}$C NMR (CDCl$_3$, 126 MHz) δ 169.6, 159.1 (d, J$_{CF}$=243.9 Hz), 155.4 (dd, J$_{CF}$=241.1, 2.5 Hz), 149.5, 137.0, 136.5, 129.2, 128.2, 127.8, 118.5 (dd, J$_{CF}$=12.6, 9.0 Hz), 117.1 (dd, J$_{CF}$=25.6, 8.7 Hz), 116.6 (dd, J$_{CF}$=24.8, 9.4 Hz), 114.5 (dd, J$_{CF}^{-1}$ 26.9, 3.9 Hz), 110.1 (d, J$_{CF}$=3.7 Hz), 41.1, 40.7, 13.4; IR (film) cm$^{-1}$ 3083, 3029, 2987, 1773, 1758, 1636, 1618, 1529, 1482, 1464, 1411, 1236, 1173, 1132, 1084, 1062, 919, 873, 813, 766, 737, 700; LRMS (ESI): Mass calcd for [M+H]$^+$ C$_{19}$H$_{15}$F$_2$N$_2$O$_2$: 341.1. found 341.3; Enantiomeric ratio was measured by chiral phase HPLC (Chiralcel OD-H; 12% IPA/hexanes 1.0 mL/min, 280 nm), Rt$_1$ (major)=14.4, Rt$_2$ (minor)=27.6 min; er=>99:1.

Example 27

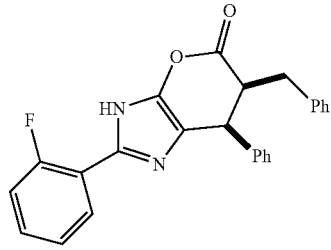 [SMILES: O=C1Oc2[nH]c(-c3ccccc3F)nc2[C@H](c2ccccc2)[C@@H]1Cc1ccccc1]

6-benzyl-2-(2-fluorophenyl)-7-phenyl-6,7-dihydropyrano[2,3-d]imidazol-5(3H)-one (5h)

Prepared according to the general procedure using (Z)-4-benzylidene-2-(2-fluorophenyl)-1H-imidazol-5(4H)-one and trans-cinnamaldehyde. After 72 h, the unpurified residue was purified by flash chromatography using 15% EtOAc/hexanes to afford 5h as an off-white solid (78 mg, 65%). Analytical data for 5 h: $^1$H NMR (500 MHz, CDCl$_3$) δ 9.32 (d, J=8.4 Hz, 1H), 8.21 (td, J=8.0, 1.9 Hz, 1H), 7.36-7.21 (m, 8H), 7.12-7.05 (m, 3H), 7.02-6.99 (m, 2H), 4.09 (d, J=6.8 Hz, 1H), 3.62 (ddd, J=10.2, 6.8, 4.6 Hz, 1H), 3.37 (dd, J=14.9, 4.5 Hz, 1H), 2.43 (dd, J=14.8, 10.2 Hz, 1H); $^{13}$C NMR (CDCl$_3$, 126 MHz) δ 169.1, 159.5 (d, J$_{CF}$=244.7 Hz), 148.8, 138.0, 137.5, 137.2, 130.1 (d, J$_{CF}$=8.9 Hz), 129.2, 129.0, 128.6, 128.5 (d, $J_{CF}$=3.0 Hz), 128.2, 128.0, 126.7, 125.2 (d, $J_{CF}$=2.9 Hz), 117.0 (d, $J_{CF}$=10.2 Hz), 115.8 (d, $J_{CF}$ 22.3 Hz), 110.3 (d, $J_{CF}$=3.3 Hz), 47.4, 38.4, 32.7; IR (film) cm$^{-1}$ 1771, 1632, 1614, 1528, 1467, 1454, 1428, 1122, 1106, 1073, 909, 762, 732, 698; LRMS (ESI): Mass calcd for [M+H]$^+$ $C_{25}H_{20}FN_2O_2$: 399.1. found 399.4; Enantiomeric ratio was measured by chiral phase HPLC (Chiralcel OD-H; 5% IPA/3% MeOH/hexanes 0.5 mL/min, 280 nm), Rt$_1$ (minor)=53.0, Rt$_2$ (major)=63.6 min; er=98:2.

Example 28

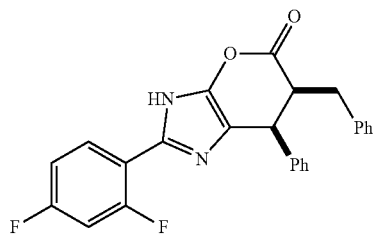 [SMILES: O=C1Oc2[nH]c(-c3ccc(F)cc3F)nc2[C@H](c2ccccc2)[C@@H]1Cc1ccccc1]

6-benzyl-2-(2,4-difluorophenyl)-7-phenyl-6,7-dihydropyrano[2,3-d]imidazol-5(3H)-one (5i)

Prepared according to the general procedure using (Z)-4-benzylidene-2-(2,4-difluorophenyl)-1H-imidazol-5(4H)-one and trans-cinnamaldehyde. After 72 h, the unpurified residue was purified by flash chromatography using 15% EtOAc/hexanes to afford 5i as an off-white solid (78 mg, 62%). Analytical data for 5i: $^1$H NMR (500 MHz, CDCl$_3$) δ 9.43 (d, J=7.1 Hz, 1H), 8.15 (td, J=9.0, 6.4 Hz, 1H), 7.35-7.27 (m, 5H), 7.26-7.23 (m, 1H), 7.11-7.05 (m, 2H), 7.01-6.92 (m, 3H), 6.83 (ddd, J=12.4, 8.4, 2.5 Hz, 1H), 4.09 (d, J=7.1 Hz, 1H), 3.61 (ddd, J=10.1, 6.9, 4.6 Hz, 1H), 3.34 (dd, J=14.9, 4.6 Hz, 1H), 2.42 (dd, J=14.8, 10.1 Hz, 1H); $^{13}$C NMR (CDCl$_3$, 126 MHz) δ 169.0, 162.6 (dd, $J_{CF}$=252.4, 12.8 Hz), 159.4 (dd, $J_{CF}$=247.4, 11.2 Hz), 148.8, 137.9, 137.2, 136.7, 129.7 (dd, $J_{CF}$=9.3, 4.8 Hz), 129.2, 129.0, 128.6, 128.3, 128.0, 126.8, 113.7 (dd, $J_{CF}$=10.6, 3.5 Hz), 112.8 (dd, $J_{CF}$=21.7, 3.1 Hz), 110.2 (d, $J_{CF}$=3.5 Hz), 104.2 (t, $J_{CF}$=26.3 Hz), 47.3, 38.4, 32.7; IR (film) cm$^{-1}$ 1771, 1632, 1597, 1535, 1494, 1448, 1267, 1138, 1124, 1105, 1090, 909, 850, 732, 697; LRMS (ESI): Mass calcd for [M+H]$^+$ $C_{25}H_{19}F_2N_2O_2$: 417.1. found 417.4; Enantiomeric ratio was measured by chiral phase HPLC (Chiralcel AD-H; 10% IPA/hexanes 1.0 mL/min, 280 nm), Rt$_1$ (minor)=25.4 Rt$_2$ (major)=30.9 min; er=98:2.

Example 29

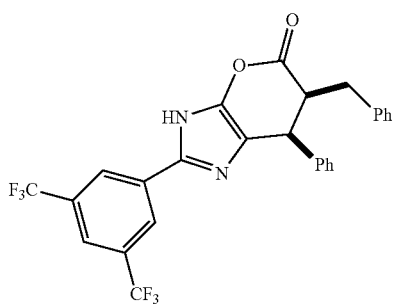 [SMILES: O=C1Oc2[nH]c(-c3cc(C(F)(F)F)cc(C(F)(F)F)c3)nc2[C@H](c2ccccc2)[C@@H]1Cc1ccccc1]

6-benzyl-2-(3,5-bis(trifluoromethyl)phenyl)-7-phenyl-6,7-dihydropyrano[2,3-d]imidazol-5(3H)-one (21)

Prepared according to the general procedure using (Z)-4-benzylidene-2-(3,5-bis(trifluoromethyl)phenyl)-1H-imidazol-5(4H)-one and trans-cinnamaldehyde. The unpurified residue was purified by flash chromatography using 15% EtOAc/hexanes to afford 21 as an off-white solid (88 mg, 57%). Analytical data for 21: $^1$H NMR (500 MHz, CDCl$_3$) δ 9.16 (s, 1H), 8.15 (s, 2H), 7.80 (s, 1H), 7.40-7.26 (m, 6H), 7.15-7.06 (m, 2H), 7.00-6.96 (m, 2H), 4.11 (d, J=6.9 Hz, 1H), 3.63 (ddd, J=10.1, 6.8, 4.6 Hz, 1H), 3.37 (dd, J=14.8, 4.7 Hz, 1H), 2.44 (dd, J=14.8, 10.1 Hz, 1H); $^{13}$C NMR (CDCl$_3$, 126 MHz) δ 168.8, 149.4, 139.0, 137.7, 136.8, 132.4 (q, $J_{CF}$=33.6 Hz), 131.2, 129.2, 129.0, 128.6, 128.4, 127.9, 126.8, 124.6 (d, $J_{CF}$=4.0 Hz), 122.9 (d, $J_{CF}$=273.0 Hz), 122.0, 112.1, 47.1, 38.5, 32.7; IR (film) cm$^{-1}$ 1780, 1641, 1618, 1528, 1401, 1361, 1279, 1186, 1133, 896, 730, 697, 682; LRMS (ESI): Mass calcd for [M+H]$^+$ $C_{27}H_{19}F_6N_2O_2$: 517.1. found 517.4; Enantiomeric ratio was measured by chiral phase HPLC (Chiralcel OD-H; 3% IPA/1% MeOH/hexanes 1.0 mL/min, 210 nm), Rt$_1$ (minor)=17.2, Rt$_2$ (major)=20.9 min; er=99:1.

Example 30

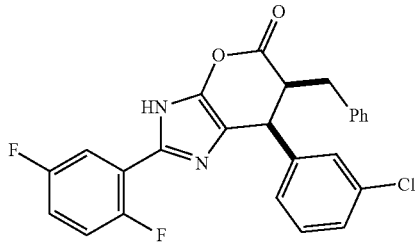 [SMILES: O=C1Oc2[nH]c(-c3cc(F)ccc3F)nc2[C@H](c2cccc(Cl)c2)[C@@H]1Cc1ccccc1]

2-(2,5-difluorophenyl)-6-(3-chlorobenzyl)-7-phenyl-6,7-dihydropyrano[2,3-d]imidazol-5(3H)-one (22)

Prepared according to the general procedure using (Z)-4-benzylidene-2-(3,5-difluorophenyl)-1H-imidazol-5(4H)-one and trans-cinnamaldehyde. The unpurified residue was purified by flash chromatography using 15% EtOAc/hexanes to afford 22 as an off-white solid (63 mg, 47%). Analytical data for 22: $^1$H NMR (500 MHz, CDCl$_3$) δ 9.41 (d, J=7.9 Hz, 1H), 7.88 (ddd, J=9.2, 6.1, 3.2 Hz, 1H), 7.34 (ap t, J=7.4 Hz, 2H), 7.31-7.24 (m, 3H), 7.11-7.03 (m, 3H), 7.01-6.95 (m, 1H), 6.92 (ap t, J=1.8 Hz, 1H), 6.87 (ap dt, J=7.0, 1.7 Hz, 1H), 4.06 (d, J=6.9 Hz, 1H), 3.63 (ddd, J=10.4, 6.9, 4.6 Hz, 1H), 3.40 (dd, J=15.0, 4.6 Hz, 1H), 2.41 (dd, J=14.9, 10.4 Hz, 1H); $^{13}$C NMR (CDCl$_3$, 126 MHz) δ 168.5, 159.1 (d, $J_{CF}$=243.8 Hz), 155.4 (d, $J_{CF}$=241.0 Hz), 149.0, 139.0, 137.4, 136.7, 134.9, 130.6, 129.0, 128.7, 128.5, 126.9, 125.9, 118.3 (dd, $J_{CF}$=12.8, 9.0 Hz), 117.1 (dd, $J_{CF}$=25.8, 8.7 Hz), 116.7 (dd, $J_{CF}$=24.8, 9.6 Hz), 114.5 (dd, $J_{CF}$=26.8, 3.6 Hz), 110.1 (d, $J_{CF}$=3.7 Hz), 46.9, 38.0, 32.7; IR (film) cm$^{-1}$ 1773, 1752, 1618, 1529, 1481, 1459, 1171, 1117, 1071; LRMS (ESI): Mass calcd for [M+H]$^+$ $C_{25}H_{18}ClF_2N_2O_2$: 451.1. found 451.4; Enantiomeric ratio was measured by chiral phase HPLC (Chiralcel AD-H; 4% IPA/2% MeOH/hexanes 0.8 mL/min, 280 nm), Rt$_1$ (major)=33.5 min, Rt$_2$ (minor)=38.5 min; er=>99:1.

Example 31

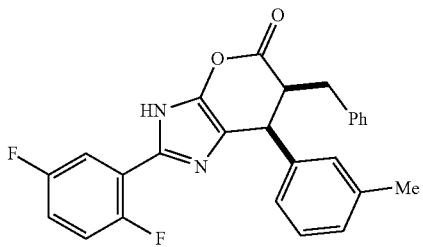 [SMILES: Cc1cccc([C@H]2c3nc(-c4cc(F)ccc4F)[nH]c3OC(=O)[C@H]2Cc2ccccc2)c1]

2-(2,5-difluorophenyl)-6-(3-methylbenzyl)-7-phenyl-6,7-dihydropyrano[2,3-d]imidazol-5(3H)-one (23)

Prepared according to the general procedure using (Z)-4-benzylidene-2-(3,5-difluorophenyl)-1H-imidazol-5(4H)-one and trans-cinnamaldehyde. The unpurified residue was purified by flash chromatography using 15% EtOAc/hexanes to afford 23 as an off-white solid (80 mg, 62%). Analytical data for 23: $^1$H NMR (500 MHz, CDCl$_3$) δ 9.35 (d, J=8.4 Hz, 1H), 7.89 (ddd, J=9.2, 6.1, 3.2 Hz, 1H), 7.35-7.30 (m, 2H), 7.28-7.24 (m, 1H), 7.22 (ap t, J=7.6 Hz, 1H), 7.14-7.08 (m, 3H), 7.08-7.02 (m, 1H), 6.99-6.93 (m, 1H), 6.81-6.77 (m, 1H), 6.76 (s, 1H), 4.05 (d, J=6.9 Hz, 1H), 3.60 (ddd, J=10.1, 6.8, 4.6 Hz, 1H), 3.36 (dd, J=14.8, 4.6 Hz, 1H), 2.43 (dd, J=14.8, 10.1 Hz, 1H), 2.31 (s, 3H); $^{13}$C NMR (CDCl$_3$, 126 MHz) δ 169.0, 159.1 (d, $J_{CF}$=243.4 Hz), 155.4 (d, $J_{CF}$=242.2 Hz), 148.9, 139.0, 138.0, 136.9, 136.3, 129.1, 129.0, 128.6, 126.7, 125.1, 118.5 (d, $J_{CF}$ 8.9 Hz), 117.1 (dd, $J_{CF}$=25.5, 8.7 Hz), 116.5 (dd, $J_{CF}$=24.8, 9.5 Hz), 114.5 (dd, $J_{CF}$=26.7, 3.5 Hz), 111.0 (d, $J_{CF}$=3.7 Hz), 47.2, 38.3, 32.7, 21.4; IR (film) cm$^{-1}$ 1773, 1637, 1618, 1529, 1481, 1460, 1235, 1170, 1117, 1071, 881, 813, 764, 750, 698; LRMS (ESI): Mass calcd for [M+H]$^+$ C$_{26}$H$_{21}$F$_2$N$_2$O$_2$: 431.2. found 431.4; Enantiomeric ratio was measured by chiral phase HPLC (Chiralcel OD-H; 5% IPA/3% MeOH/hexanes 0.5 mL/min, 280 nm), Rt$_1$ (minor)=40.0, Rt$_2$ (major)=44.8 min; er=99:1.

Example 32

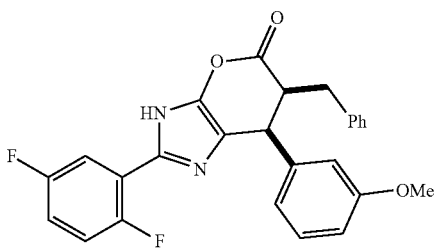 [SMILES: COc1cccc([C@H]2c3nc(-c4cc(F)ccc4F)[nH]c3OC(=O)[C@H]2Cc2ccccc2)c1]

2-(2,5-difluorophenyl)-6-(3-methoxybenzyl)-7-phenyl-6,7-dihydropyrano[2,3-d]imidazol-5(3H)-one (24)

Prepared according to the general procedure using (Z)-4-benzylidene-2-(3,5-difluorophenyl)-1H-imidazol-5(4H)-one and trans-cinnamaldehyde. The unpurified residue was purified by flash chromatography using 15% EtOAc/hexanes to afford 24 as an off-white solid (91 mg, 68%). Analytical data for 24: $^1$H NMR (500 MHz, CDCl$_3$) δ 9.37 (d, J=8.0 Hz, 1H), 7.92 (ddd, J=9.2, 6.1, 3.3 Hz, 1H), 7.38-7.32 (m, 2H), 7.32-7.26 (m, 2H), 7.14 (ap d, J=7.2 Hz, 2H), 7.08 (ddd, J=11.3, 8.9, 4.3 Hz, 1H), 7.03-6.96 (m, 1H), 6.87 (ddd, J=8.3, 2.6, 0.9 Hz, 1H), 6.63 (ap d, J=7.6 Hz, 1H), 6.53 (ap t, J=2.1 Hz, 1H), 4.08 (d, J=6.9 Hz, 1H), 3.79 (s, 3H), 3.62 (ddd, J=10.2, 6.8, 4.5 Hz, 1H), 3.41 (dd, J=14.8, 4.5 Hz, 1H), 2.49 (dd, J=14.9, 10.2 Hz, 1H); $^{13}$C NMR (CDCl$_3$, 126 MHz) δ 168.9, 160.0, 159.2 (d, $J_{CF}$=240.4 Hz), 157.3 (d, $J_{CF}$=228.8 Hz), 149.0, 138.6, 138.0, 136.4, 130.4, 129.1, 128.6, 126.8, 120.1, 118.4 (dd, $J_{CF}$=12.6, 9.5 Hz), 117.1 (dd, $J_{CF}$=25.8, 8.7 Hz), 116.6 (dd, $J_{CF}$=24.5, 10.0 Hz), 114.5 (dd, $J_{CF}$=26.8, 3.7 Hz), 113.7; 113.6, 110.9 (d, $J_{CF}$=3.7 Hz), 55.2, 47.3, 38.4, 32.7; IR (film) cm$^{-1}$ 1772, 1636, 1619, 1529, 1482, 1237, 1171, 1117, 1071, 729, 698; LRMS (ESI): Mass calcd for [M+H]$^+$ C$_{26}$H$_{21}$F$_2$N$_2$O$_3$: 447.1. found 447.4; Enantiomeric ratio was measured by chiral phase HPLC (Chiralcel AD-H; 4% IPA/3% MeOH/hexanes; 0.5 mL/min, 280 nm), Rt$_1$ (minor)=76.8, Rt$_2$ (major)=85.4 min; er=92:8.

Example 33

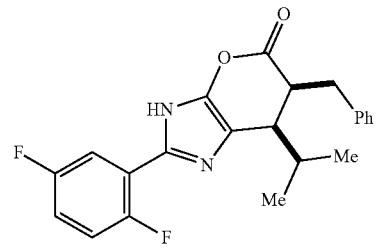 [SMILES: CC(C)[C@H]1c2nc(-c3cc(F)ccc3F)[nH]c2OC(=O)[C@H]1Cc1ccccc1]

6-benzyl-2-(2,5-difluorophenyl)-7-isopropyl-6,7-dihydropyrano[2,3-d]imidazol-5(3H)-one (25)

Prepared according to the general procedure using (Z)-2-(2,5-difluorophenyl)-4-(2-methylpropylidene)-1H-imidazol-5(4H)-one and trans-cinnamaldehyde. The unpurified residue was purified by flash chromatography using 15% EtOAc/hexanes to afford 25 as an off-white solid (84 mg, 73%). Analytical data for 25: $^1$H NMR (500 MHz, CDCl$_3$) δ 9.31 (d, J=7.2 Hz, 1H), 7.88 (ddd, J=9.2, 6.1, 3.2 Hz, 1H), 7.38-7.29 (m, 3H), 7.29-7.22 (m, 2H), 7.09 (ddd, J=11.5, 9.1, 4.2 Hz, 1H), 7.03-6.94 (m, 1H), 3.57 (dd, J=14.6, 4.7 Hz, 1H), 3.24 (ddd, J=11.1, 6.7, 4.7 Hz, 1H), 2.93-2.79 (m, 2H), 2.23 (ddt, J=10.3, 6.9, 5.1 Hz, 1H), 0.93 (d, J=6.8 Hz, 3H), 0.77 (d, J=6.7 Hz, 3H); $^{13}$C NMR (CDCl$_3$, 126 MHz) δ 170.4, 159.2 (d, $J_{CF}$=243.6 Hz), 155.4 (dd, $J_{CF}$=240.3, 2.1 Hz), 150.2, 138.3, 136.0, 128.8, 128.7, 126.8, 118.5 (dd, $J_{CF}$=12.7, 9.2 Hz), 117.1 (dd, $J_{CF}$=25.8, 8.7 Hz), 116.4 (dd, $J_{CF}$=24.9, 9.5 Hz), 114.4 (dd, $J_{CF}$=26.9, 3.9 Hz), 108.0 (d, $J_{CF}$=3.7 Hz), 45.6, 37.6, 32.5, 27.2, 21.8, 15.5; IR (film) cm$^{-1}$ 2964, 2932, 2874, 1769, 1616, 1528, 1481, 1458, 1370, 1237, 1173, 1121, 1067, 766, 734, 698; LRMS (ESI): Mass calcd for [M+H]$^+$ C$_{22}$H$_{21}$F$_2$N$_2$O$_2$: 383.2. found 383.3; Enantiomeric ratio was measured by chiral phase HPLC (Chiralcel OD-H, 20% IPA/Hexanes, 1.0 mL/min, 280 nm), Rt$_1$ (minor)=13.6 min, Rt$_2$ (major)=20.2 min; er=>99:1.

Example 34

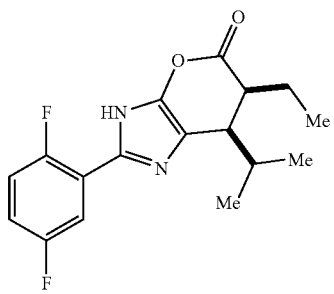 [SMILES: CC[C@@H]1C(=O)Oc2[nH]c(-c3cc(F)ccc3F)nc2[C@@H]1C(C)C]

2-(2,5-difluorophenyl)-6-ethyl-7-isopropyl-6,7-dihydropyrano[2,3-d]imidazol-5(3H)-one (26)

Prepared according to the general procedure using (Z)-2-(2,5-difluorophenyl)-4-(2-methylpropylidene)-1H-imidazol-5(4H)-one and crotonaldehyde. The unpurified residue was purified by flash chromatography using 15% EtOAc/hexanes to afford 26 as an off-white solid (57 mg, 59%). Analytical data for 26: $^1$H NMR (500 MHz, CDCl$_3$) δ $^1$H NMR (500 MHz, CDCl$_3$) δ 9.39 (s, 1H), 7.90 (ddd, J=9.2, 6.2, 3.2 Hz, 1H), 7.12 (ddd, J=11.4, 9.0, 4.2 Hz, 1H), 7.04-6.94 (m, 1H), 3.12 (dd, J=6.9, 3.5 Hz, 1H), 2.80-2.69 (m, 1H), 2.25-2.12 (m, 1H), 2.12-2.03 (m, 1H), 1.69-1.58 (m, 1H), 1.08 (t, J=7.4 Hz, 3H), 1.03 (d, J=6.9 Hz, 3H), 0.70 (d, J=6.8 Hz, 3H); $^{13}$C NMR (CDCl$_3$, 126 MHz) δ 170.7, 159.2 (d, J$_{CF}$=243.1 Hz), 155.4 (dd, J$_{CF}$=240.4, 2.1 Hz), 150.3, 136.0, 118.6 (dd, J$_{CF}$=12.4, 9.0 Hz), 117.1 (dd, J$_{CF}$=25.7, 8.7 Hz), 116.3 (dd, J$_{CF}$=24.8, 9.5 Hz), 114.5 (dd, J$_{CF}$=26.8, 3.9 Hz), 108.0 (d, J$_{CF}$=3.8 Hz), 45.3, 38.5, 27.1, 21.9, 20.0, 15.7, 12.1; IR (film) cm$^{-1}$ 2965, 2935, 2877, 1759, 1636, 1529, 1482, 1460, 1175, 1142, 1115, 1066, 813, 766; LRMS (ESI): Mass calcd for [M+H]$^+$ C$_{17}$H$_{19}$F$_2$N$_2$O$_2$: 321.1. found 321.3; Enantiomeric ratio was measured by chiral phase HPLC (Chiralcel OD-H, 20% IPA/Hexanes, 0.8 mL/min, 280 nm), Rt (major)=7.6 min, Rt (minor)=10.6 min; er=>99:1.

Example 35

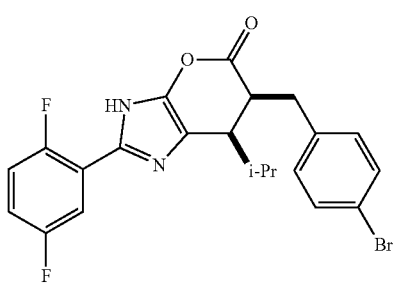 [SMILES: CC(C)[C@H]1c2nc(-c3cc(F)ccc3F)[nH]c2OC(=O)[C@H]1Cc1ccc(Br)cc1]

6-(4-bromobenzyl)-2-(2,5-difluorophenyl)-7-isopropyl-6,7-dihydropyrano[2,3-d]imidazol-5(3H)-one (27)

Prepared according to the general procedure using (Z)-2-(2,5-difluorophenyl)-4-(2-methylpropylidene)-1H-imidazol-5(4H)-one and (E)-3-(4-bromophenyl)acrylaldehyde. The unpurified residue was purified by flash chromatography using 15% EtOAc/hexanes to afford 27 as an off-white solid (122 mg, 88%). Analytical data for 27: $^1$H NMR (500 MHz, CDCl$_3$) δ 9.32 (d, J=8.4 Hz, 1H), 7.88 (ddd, J=9.2, 6.1, 3.2 Hz, 1H), 7.46 (d, J=8.4 Hz, 2H), 7.15 (d, J=8.3 Hz, 2H), 7.10 (ddd, J=11.4, 9.1, 4.3 Hz, 1H), 7.02-6.96 (m, 1H), 3.50 (dd, J=14.7, 5.1 Hz, 1H), 3.20 (ddd, J=10.1, 6.7, 5.1 Hz, 1H), 2.87 (dd, J=6.8, 3.5 Hz, 1H), 2.82 (dd, J=14.7, 10.1 Hz, 1H), 2.16 (ddt, J=10.3, 6.8, 3.5 Hz, 1H), 0.95 (d, J=6.9 Hz, 3H), 0.76 (d, J=6.7 Hz, 3H); $^{13}$C NMR (CDCl$_3$, 126 MHz) δ 170.1, 159.2 (d, J$_{CF}$=243.4 Hz), 155.4 (d, J$_{CF}$=240.7 Hz), 150.2, 137.3, 136.2, 131.9, 130.4, 120.6, 118.5 (dd, J$_{CF}$=12.3, 9.2 Hz), 117.1 (dd, J$_{CF}$=25.9, 8.7 Hz), 116.5 (dd, J$_{CF}$=24.7, 9.8 Hz), 114.5 (dd, J$_{CF}$=27.0, 3.7 Hz), 107.8 (d, J$_{CF}$=3.8 Hz), 45.4, 37.8, 32.1, 27.3, 21.8, 15.5; IR (film) cm$^{-1}$ 2964, 2934, 1760, 1616, 1529, 1482, 1460, 1348, 1237, 1173, 1125, 1071, 1028, 812, 766, 736, 703; LRMS (ESI): Mass calcd for [M+H]$^+$ C$_{22}$H$_{20}$BrF$_2$N$_2$O$_2$: 461.1. found 461.2; Enantiomeric ratio was measured by chiral phase HPLC (Chiralcel OD-H, 20% IPA/Hexanes, 1.0 mL/min, 280 nm), Rt (major)=21.2 min, Rt (minor)=25.9 min; er=>99:1.

Example 36

Representative Ring Opening

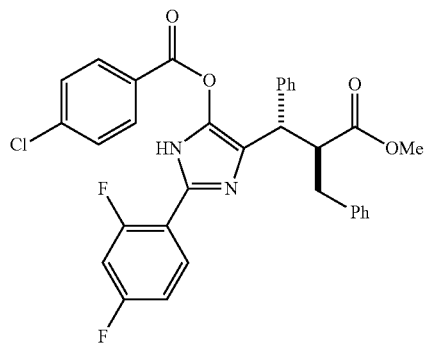 [SMILES: COC(=O)[C@@H](Cc1ccccc1)[C@@H](c1ccccc1)c1nc(-c2ccc(F)cc2F)[nH]c1OC(=O)c1ccc(Cl)cc1]

4-((1S,2S)-2-benzyl-3-methoxy-3-oxo-1-phenylpropyl)-2-(2,4-difluorophenyl)-1H-imidazol-5-yl-4-chlorobenzoate (28)

To lactone 5i (425 mg, 1.02 mmol) in a 2 dram vial with a septa cap was added a solution of 5% formic acid in methanol (5.0 mL). The reaction was heated to 65° C. and stirred for 12 hours. The resulting solid was collected by vacuum filtration, washing with MeOH and hexanes and dried under vacuum for several hours to afford the imidazolidinone as a white solid (322 mg, 70%). The crude imidazolidinone was used without further purification in subsequent transformations.

To the imidazolidinone (85 mg, 0.190 mmol) in THF (3.8 mL) was added triethylamine (40 μl, 0.284 mmol) and 4-chlorobenzoyl chloride (33 mg, 0.190 mmol). The reaction was stirred at 23° C. for 1 hour, at which time the reaction was diluted with dichloromethane and quenched with water. The aqueous layer was extracted with dichloromethane (2×10 mL) and the combined organic layers were dried over sodium sulfate and concentrated under reduced pressure. The unpurified residue was purified by flash chromatography using 10% EtOAc/hexanes to afford 28 as an off-white solid (105 mg, 94%). Analytical data for 28: $^1$H NMR (500 MHz, CDCl$_3$) δ 10.16 (d, J=7.0 Hz, 1H), 8.15 (td, J=9.0, 6.3 Hz, 1H), 8.03 (d, J=8.5 Hz, 2H), 7.46 (d, J=8.5 Hz, 2H), 7.30-7.23 (m, 4H), 7.24-7.18 (m, 3H), 7.18-7.11 (m, 1H), 7.10 (ap d, J=6.8 Hz, 2H), 7.01-6.87 (m, 2H), 4.34 (d, J=7.8 Hz, 1H), 3.46 (q, J=7.7 Hz, 1H), 3.37 (s, 3H), 3.03 (d, J=7.7 Hz, 2H); $^{13}$C NMR (CDCl$_3$, 126 MHz) δ 174.4, 163.8, 162.6 (dd, $J_{CF}$=252.2, 12.8 Hz), 159.5 (dd, $J_{CF}$=248.2, 12.0 Hz), 143.4, 140.3, 138.7, 138.3, 136.7, 131.7, 129.6 (dd, $J_{CF}$=9.6, 4.7 Hz), 128.9, 128.8, 128.7, 128.5, 127.9, 127.5, 127.1, 126.5, 118.0 (d, $J_{CF}$=3.2 Hz), 113.9 (dd, $J_{CF}$=10.5, 3.8 Hz), 112.5 (dd, $J_{CF}$=21.6, 3.1 Hz), 104.2 (t, $J_{CF}$=26.1 Hz), 51.9, 51.8, 43.3, 36.9; IR (film) cm$^{-1}$ 1749, 1625, 1592, 1535, 1496, 1488, 1455, 1433, 1400, 1364, 1307, 1284, 1267, 1253, 1232, 1190, 1140, 1092, 1064, 1013, 976, 908, 846753, 735, 702; LRMS (ESI): Mass calcd for [M+H]$^+$ C$_{33}$H$_{26}$ClF$_2$N$_2$O$_4$: 587.2. found 587.3.

We claim:

1. A method of preparing a bicyclic lactone compound, said method
comprising: providing a mixture of a heterocyclic alkylidene imidazolidinone, a triazolium N-heterocyclic carbene catalyst precursor compound and a base component, said alkylidene imidazolidinone of a formula

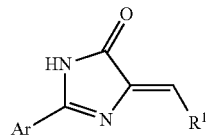

wherein Ar is selected from aryl and substituted aryl moieties, said Ar substituents selected from alkyl, alkoxy, halo and haloalkyl substituents and combinations thereof, and R$^1$ is selected from aryl, substituted aryl, heteroaryl, substituted heteroaryl, alkyl and cycloalkyl moieties, said R$^1$ substituents selected from alkyl, alkoxy, halo and haloalkyl substituents and combinations thereof; and
introducing to said mixture an α,β-unsaturated aldehyde in the presence of an acid component, said aldehyde of a formula

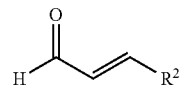

wherein R$^2$ is selected from H, alkyl, cycloalkyl, aryl, substituted aryl, heteroaryl and substituted heteroaryl moieties, said R$^2$ substituents selected from alkyl, alkoxy and halo substituents and combinations thereof, to provide a bicyclic lactone compound of a formula or a salt thereof

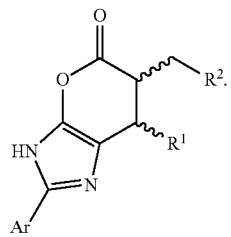

2. The method of claim 1 wherein said acid component is acetic acid.

3. The method of claim 2 wherein said base component is an acetate.

4. The method of claim 3 wherein said base component is an ammonium acetate.

5. The method of claim 1 wherein Ar is substituted aryl and a said Ar substituent is selected from fluoro- and chloro-substituents.

6. The method of claim 5 wherein a said substituent is at an ortho-position on said aryl moiety.

7. A method of using a heterocyclic conjugate acceptor component to prepare a bicyclic lactone compound of a formula

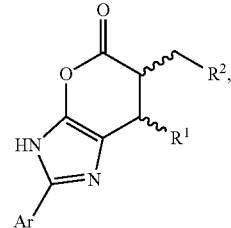

said method comprising:
providing a mixture of a heterocyclic alkylidene imidazolidinone, a triazolium N-heterocyclic carbene catalyst precursor compound and a base component, said alkylidene imidazolidinone of a formula

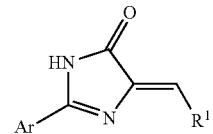

wherein Ar is selected from aryl and substituted aryl moieties, said Ar substituents selected from alkyl, alkoxy, halo and haloalkyl substituents and combinations thereof, and R$^1$ is selected from aryl, substituted aryl, heteroaryl, substituted heteroaryl, alkyl and cycloalkyl moieties, said R$^1$ substituents selected from alkyl, alkoxy, halo and haloalkyl substituents and combinations thereof;
introducing to said mixture an α,β-unsaturated aldehyde in the presence of an acid component, said aldehyde of a formula

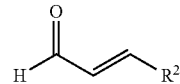

wherein R$^2$ is selected from H, alkyl, cycloalkyl, aryl, substituted aryl, heteroaryl, substituted heteroaryl moieties, said R$^2$ substituents selected from alkyl, alkoxy and halo substituents and combinations thereof, to couple said components; and
intramolecular O-acylation of said imidazolidinone to provide said bicyclic lactone compound or a salt thereof.

8. The method of claim 7 wherein said acid component is acetic acid.

9. The method of claim 8 wherein said base component is an acetate.

10. The method of claim 9 wherein said base component is an ammonium acetate.

11. The method of claim 7 wherein Ar is substituted aryl and a said Ar substituent is selected from fluoro- and chloro-substituents.

12. The method of claim 11 wherein a said substituent is at an ortho-position on said aryl moiety.

13. A compound selected from compounds of a formula

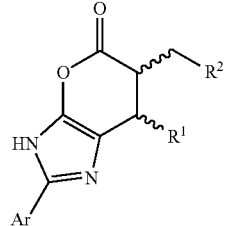

wherein Ar is selected from aryl and substituted aryl moieties, said Ar substituents selected from alkyl, alkoxy, halo and haloalkyl substituents and combinations thereof; $R^1$ is selected from aryl, substituted aryl, heteroaryl, substituted heteroaryl, alkyl and cycloalkyl moieties, said $R^1$ substituents selected from alkyl, alkoxy, halo and haloalkyl substituents and combinations thereof; and $R^2$ is selected from H, alkyl, cycloalkyl, aryl, substituted aryl, heteroaryl and substituted heteroaryl moieties, said $R^2$ substituents selected from alkyl, alkoxy and halo substituents and combinations thereof, and salts thereof.

14. The compound of claim 13 wherein Ar is substituted aryl and a said Ar substituent is selected from fluoro- and chloro-substituents.

15. The compound of claim 14 wherein a said substituent is at an ortho-position on said aryl moiety.

16. The compound of claim 13 enantioenriched with a cis-diastereomer.

17. A compound selected from compounds of a formula

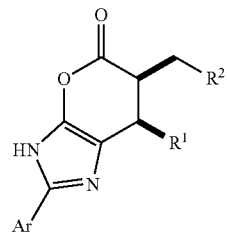

wherein Ar is selected from aryl and substituted aryl moieties, said Ar substituents selected from alkyl, alkoxy, halo and haloalkyl substituents and combinations thereof; $R^1$ is selected from aryl, substituted aryl, heteroaryl, substituted heteroaryl, alkyl and cycloalkyl moieties, said $R^1$ substituents selected from alkyl, alkoxy, halo and haloalkyl substituents and combinations thereof; and $R^2$ is selected from H, alkyl, cycloalkyl, aryl, substituted aryl, heteroaryl and substituted heteroaryl moieties, said $R^2$ substituents selected from alkyl, alkoxy and halo substituents and combinations thereof, and salts thereof.

18. The compound of claim 17 wherein Ar is substituted aryl and a said Ar substituent is selected from fluoro- and chloro-substituents.

19. The compound of claim 18 wherein a said substituent is at an ortho-position on said aryl moiety.

20. The compound of claim 19 enantioenriched with a cis-diastereomer.

* * * * *